United States Patent
Mizuta et al.

(10) Patent No.: US 12,242,083 B2
(45) Date of Patent: Mar. 4, 2025

(54) OPTICAL UNIT, OPTICAL DEVICE, AND IMAGE DISPLAY SYSTEM

(71) Applicant: NIKON CORPORATION, Tokyo (JP)

(72) Inventors: Masahiro Mizuta, Yokohama (JP);
Ryoichi Sataka, Yokohama (JP);
Tomohiro Kawasaki, Saitama (JP)

(73) Assignee: NIKON CORPORATION, Tokyo (JP)

( * ) Notice: Subject to any disclaimer, the term of this patent is extended or adjusted under 35 U.S.C. 154(b) by 855 days.

(21) Appl. No.: 17/338,850

(22) Filed: Jun. 4, 2021

(65) Prior Publication Data
US 2021/0294117 A1 Sep. 23, 2021

Related U.S. Application Data

(63) Continuation of application No. PCT/JP2018/044780, filed on Dec. 5, 2018.

(51) Int. Cl.
*G02B 30/36* (2020.01)
*A61B 3/13* (2006.01)

(52) U.S. Cl.
CPC .............. *G02B 30/36* (2020.01); *A61B 3/13* (2013.01)

(58) Field of Classification Search
None
See application file for complete search history.

(56) References Cited

U.S. PATENT DOCUMENTS

| | | | |
|---|---|---|---|
| 5,926,321 A * | 7/1999 | Shikama | G02B 27/0172 359/644 |
| 5,978,015 A | 11/1999 | Ishibashi et al. | |
| 2017/0185109 A1 | 6/2017 | Tatsuta | |
| 2018/0314063 A1 | 11/2018 | Yatsu et al. | |

FOREIGN PATENT DOCUMENTS

| | | |
|---|---|---|
| JP | 8-126031 A | 5/1996 |
| JP | 11-9554 | 1/1999 |
| JP | 2004-329762 A | 11/2004 |
| JP | 2006-284877 A | 10/2006 |
| JP | 2016-87173 A | 5/2016 |
| JP | 2017-118286 A | 6/2017 |
| KR | 11-9554 | 1/1999 |
| WO | WO 2017/061039 A1 | 4/2017 |

OTHER PUBLICATIONS

Office Action dated Dec. 6, 2022, in Japanese Application No. 2020-558737.
International Search Report dated Mar. 5, 2019, in corresponding International Patent Application No. PCT/JP2018/044780.
(Continued)

*Primary Examiner* — Robert E. Tallman
(74) *Attorney, Agent, or Firm* — STAAS & HALSEY LLP

(57) ABSTRACT

An optical unit includes an optical system that includes a focal point on an incident side of light at a position for setting a display image of an object and that is configured to emit light from a focal plane as parallel light. The optical unit also includes a housing section housing the optical system and is configured so as to satisfy a condition equation expressed by $IB \geq 7570$ mm$^3$ wherein IB is a viewable area where the display image is viewable.

16 Claims, 23 Drawing Sheets

(56) References Cited

OTHER PUBLICATIONS

Written Opinion of the International Searching Authority dated Mar. 5, 2019, in corresponding International Patent Application No. PCT/JP2018/044780.
AmadeusSVX, HoloLens optical systems: slideshare [online],2018, 01 months, 05months, 85758620 days, and 28 days, and mainly refer to the slide URL:https://www.slideshare.net/AmadeusSVX/hololens and the slide 11, 19, 22, 24, 27. [Search on May 2, 2022].
Office Action dated May 17, 2022, in Japanese Patent Application No. 2020-558737.

* cited by examiner

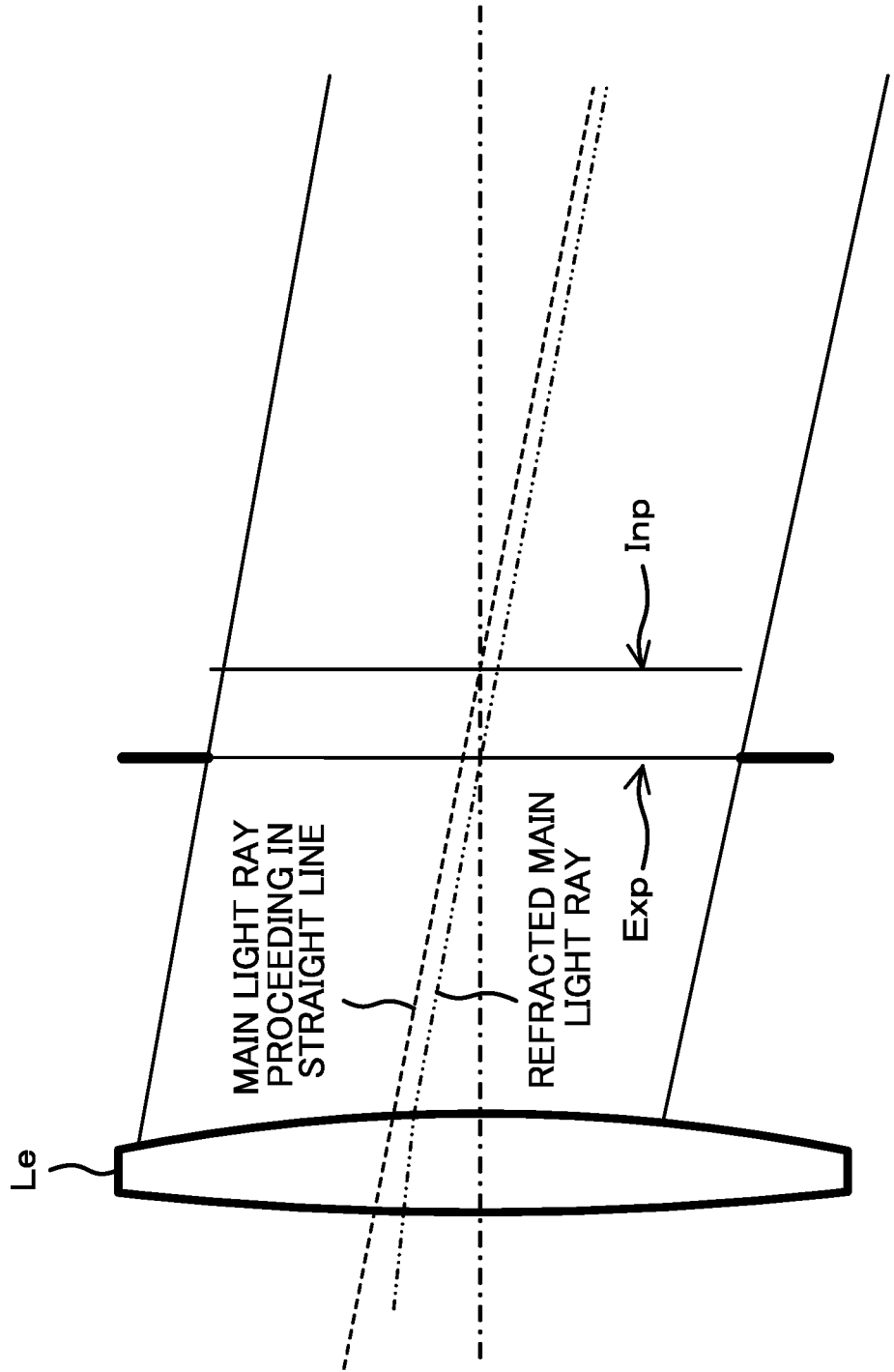

ExpL  ExpR 42L  42R

OPTICAL UNIT, OPTICAL DEVICE, AND IMAGE DISPLAY SYSTEM

CROSS-REFERENCE TO RELATED APPLICATION

This application is a continuation application of International Application No. PCT/JP2018/044780, filed Dec. 5, 2018, the disclosure of which is incorporated herein by reference in its entirety.

TECHNICAL FIELD

The present disclosure relates to an optical unit, an optical device, and an image display system.

BACKGROUND ART

In ophthalmology there are various implementations of ophthalmic devices capable of observing the eyes of subjects (hereafter referred to as subject eyes) for the purpose of ophthalmic diagnostics and surgical treatment of the eyes. One known example of an ophthalmic device is a surgical microscope configured to allow the microscope to move with respect to a subject eye to increase the degrees of freedom for an observer to observe the subject eye (see Japanese Patent Application Laid-Open (JP-A) No. 2004-329762).

SUMMARY OF INVENTION

A first aspect of the present disclosure is an optical unit including an optical system that includes a focal point on an incident side of light at a position for setting a display image of an object and that is configured to emit light from a focal plane as parallel light. The optical unit also includes a housing section to house the optical system. The optical unit is configured so as to satisfy a condition equation expressed by $IB \geq 7570$ mm$^3$, wherein IB is a viewable area where the display image is viewable.

A second aspect of the present disclosure is an optical unit including an optical system that includes a focal point on an incident side of light at a position for setting a display image of an object and that is configured to emit light from a focal plane as parallel light. The optical system is provided with a lens group including a first lens and a second lens and is configured so as to satisfy a condition equation expressed by $d1/d2 > 0.5$, wherein d1 is a distance from an end portion of the first lens disposed on the incident side to an end portion of a second lens disposed on an exit side of the light, and d2 is a distance from a position where the display image is set to the end portion of the second lens on the light exit side.

A third aspect of the present disclosure is an optical unit including an optical system that includes a focal point on an incident side of light at a position for setting a display image of an object and that is configured to emit light from a focal plane as parallel light. The optical system is provided with a lens group including a first lens and a second lens. The optical system is formed such that a chief light ray incident to the first lens at a maximum angle of view from light of the display image pass through at positions at a greater diameter than ½ an effective diameter of the first lens.

A fourth aspect of the present disclosure is an optical device including plural of the optical units.

A fifth aspect of the present disclosure is an optical device including a left-side optical system, a right-side optical system, and a housing section. The left-side optical system includes a focal point on an incident side of light at a position for setting a left-eye display image as a display image of an object, and is configured to emit light from a focal plane as parallel light and to form a left-eye viewable area where the left-eye display image is viewable. The right-side optical system includes a focal point on an incident side of light at a position for setting a right-eye display image different to the left-eye display image, and is configured to emit light from a focal plane as parallel light and to form a right-eye viewable area where the right-eye display image is viewable. The housing section houses the left-side optical system and the right-side optical system. The optical device is configured in at least one optical system from out of the left-side optical system or the right-side optical system so as to satisfy a condition equation expressed by $d1/d2 > 0.5$, wherein d1 is a distance from an end portion of a lens surface on an incident side of light to an end portion of a lens surface on an exit side, and d2 is a distance from a position of the display image to the end portion of the lens surface on the light exit side.

A sixth aspect of the present disclosure is an image display system including the optical device, an imaging section configured to image the object, and an arm section on which the imaging section is disposed.

A seventh aspect of the present disclosure is an image display system including an imaging section configured to image an object, plural optical devices configured by the optical device, and an installation section configured to install the plural optical devices so as to be capable of moving independently.

BRIEF DESCRIPTION OF DRAWINGS

FIG. 9B is an enlarged diagram of a pupil periphery according to an exemplary embodiment.

DESCRIPTION OF EMBODIMENTS

Figure 1:
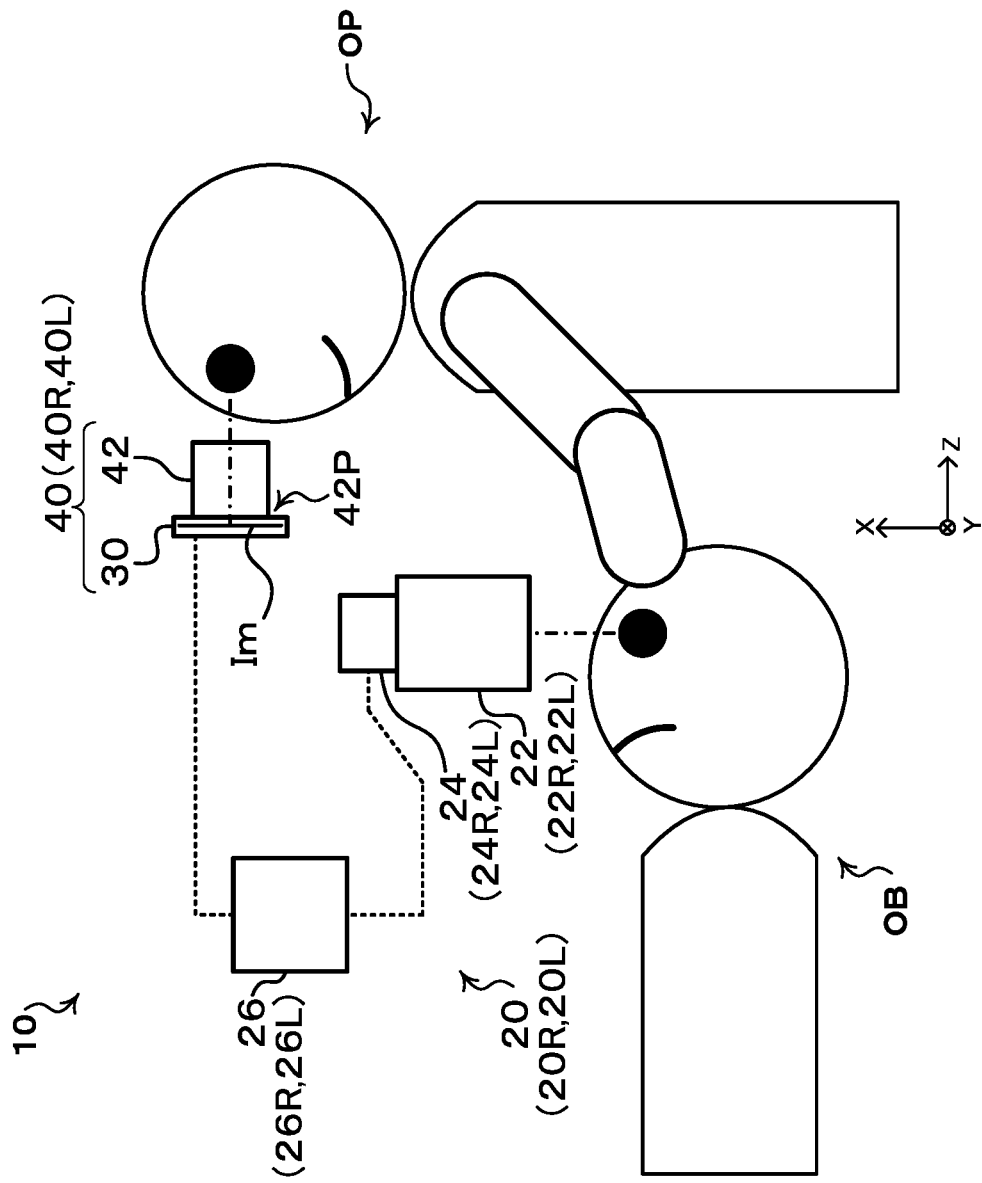
FIG. 1 is a block diagram illustrating an example of an overall configuration of an ophthalmic system according to an exemplary embodiment.

Explanation follows regarding an example of an exemplary embodiment of technology disclosed herein, with reference to the drawings.

The present disclosure is applicable to any device for displaying images, and may also be applied to a system equipped with a device for displaying images (such as an image display system). In the present exemplary embodiment, for ease of explanation, a case will be described in which the present disclosure is applied to an ophthalmic system for an observer such as a doctor to observe an eye (subject eye) of a patient or the like and to observe the periphery of the subject eye for the purpose in ophthalmology of ophthalmic diagnostics (or examination) and surgical treatment of the eyes (such as ophthalmic surgery). Note that in the drawings, configuration elements and parts the same as or equivalent to one another are allocated the same reference numerals. Moreover, the proportions in the drawings may be exaggerated for ease of explanation and may differ from actual proportions. Note that in the present exemplary embodiment, the eye of a patient or the like serves as an example of an object.

The image display system according to the present disclosure is not limited to an ophthalmic system applied to an ophthalmic device. Namely, there is no limitation to an image display device to display an image imaged by an imaging device employed in ophthalmology to image a subject eye and a periphery of the subject eye, and application may be made to any image display device and image display system in which an object is imaged, without limitation to ophthalmology, and the imaging image displayed (for example a medical image display device employed in examination or surgery). For example, in fields of medicine, application may be made to image display devices and image display systems employed in any field of medicine (for example neurosurgery). Moreover, the image display system according to the present disclosure is not limited to an image display device or image display system employed in any medical field, and is obviously applicable to any image display device and image display system capable of displaying images. Note that in the present specification "ophthalmology" refers to the medical field relating to the eyes.

Moreover, the image (display image) employed in the image display system according to the present disclosure may be a still image, or may be a video image. Moreover, the images employed in the image display system according to the present disclosure are not limited to imaging images. Namely, employing an image imaged by an imaging device as the imaging image is merely an example of the present disclosure. For example, the present disclosure is also applicable to an image display device and an image display system for displaying pre-prepared images.

As an example of an image display system according to the present disclosure, an example will be described of a surgical image display system (for example a system including an ophthalmic surgical microscope) employed when an observer such as a doctor operates while observing the subject eye and the periphery of the subject eye of a patient or the like as an example of application to an ophthalmic system. The application in this case to an ophthalmic surgical microscope is also merely an example of an image display system according to the present disclosure, and in medical fields, application may be made to surgical microscopes employed in any field of medicine. The image display system according to the present disclosure is also not limited to a surgical microscope employed in a medical field, and obviously application may be made to another optical device including a microscope for observing objects.

FIG. 1 illustrates an example of a configuration of an ophthalmic system 10 according to an exemplary embodiment of the present disclosure.

As illustrated in FIG. 1, the ophthalmic system 10 includes an imaging section 20 to image the subject eye and periphery of the subject eye as an object OB, and an image display device 40 used to display the imaging images that have been imaged with the imaging section 20 to an observer OP. The image display device 40 includes a display section 30 such as a liquid crystal or organic EL display to display imaging images that have been imaged with the imaging section 20, and an optical unit 42 to present the imaging image by display on the display section 30 to the observer OP. Note that the image display device 40 of the present exemplary embodiment is an example of an optical device equipped with the display section 30 and the optical unit 42.

The display section 30 such as a display is detachably attached to the optical unit 42 in the image display device 40. An attachment mechanism 42P is provided to a portion of the optical unit 42 on the light-incident side. The attachment mechanism 42P is an example of an attachment section used to attach and detach a display section to the optical unit 42. The image display device 40 is formed by the display section 30 being attached to the optical unit 42. In the ophthalmic system 10 according to the present exemplary embodiment, the imaging section 20 is formed independently to the image display device 40 provided with the display section 30, and the imaging section 20 and the image display device 40 are capable of moving separately to each other.

The ophthalmic system 10 according to the present exemplary embodiment will be described with reference to an example of a case in which the observer OP (for example a doctor, assistant, or researcher) views (with binocular vision) the eye (subject eye) and the periphery of the subject eye that is the object OB using both eyes of the observer OP. Note that stereopsis is an example of binocular vision. The stereopsis-type ophthalmic system 10 independently forms a right-side optical path of an image to be displayed for the right eye of the observer OP, and a left-side optical path of an image to be displayed for the left eye of the observer OP. For example, the left-side optical path and the right-side optical path are arranged at the left and right eyes of the observer OP so as to be separated along a specific direction corresponding to an inter-pupil direction of the observer OP. From the perspective of the observer OP, the right-side optical path is disposed on the right side and the left-side optical path is disposed on the left side. Note that when discriminating between the right eye and the left eye in the following explanation, configuration elements for the right eye will be given the suffix R, and configuration elements for the left eye will be given the suffix L. The suffixes R, L will be omitted when this discrimination is not made. Moreover, in the following explanation, an inter-pupil direction of the observer OP when the ophthalmic system 10 is installed on a horizontal plane is denoted the "Y direction", a vertical direction with respect to the horizontal plane is denoted the "X direction", and a direction in which light approaches the observer OP when the observer OP views an image of the object OB and that is orthogonal to both the X direction and the Y direction is denoted the "Z direction".

The imaging section 20 is equipped with a microscope 22, a camera 24, and a camera controller 26. The microscope 22 includes an optical system for observation by the observer OP or the like of the object OB, i.e. the subject eye and the periphery of the subject eye. The camera 24 is an electronic device for converting images from the microscope 22 of the object OB, i.e. the subject eye and the periphery of the subject eye, into a picture signal. The camera controller 26 is an electronic device for converting the picture signal into a display signal. The camera controller 26 is connected to the display section 30, and outputs a display signal to the display section 30. The images imaged by the camera 24 are thereby formed on the display section 30 as imaging images (display images) Im.

In the present exemplary embodiment, in order to obtain an image for display to the right eye of the observer OP and an image for display to the left eye of the observer OP, the imaging section 20 includes a right-eye imaging section 20R and a left-eye imaging section 20L. More specifically, the imaging section 20 includes a right-eye microscope 22R and a left-eye microscope 22L, and a right-eye camera 24R and a left-eye camera 24L. The controller 26 may be configured by an independent right-eye controller 26R and left-eye controller 26L, or the controller 26 may be configured as a single unit. In cases in which a single controller 26 is employed, picture signals from the right-eye camera 24R and the left-eye camera 24L are each subjected to image processing so as to respectively output an image processed right-eye display signal and an image processed left-eye display signal to a right-eye display section 30R and a left-eye display section 30L, described later. Note that instead of using two microscopes (22R, 22L), the microscope 22 may be configured to form a parallax image (3D image) for stereoscopy using a single microscope 22 without providing the two microscopes (22R, 22L). Moreover, in cases in which a 3D image is not displayed, the microscope 22 may display a 2D image of the object OB. Since the imaging section 20 of the present exemplary embodiment has a similar configuration for both the right eye and the left eye, individual explanations thereof will be omitted.

In the ophthalmic system 10 according to the present exemplary embodiment, signal sending and receiving (for example when exchanging image data) may be implemented either by wireless communication or wired communication. For example, communication between the camera 24, the camera controller 26, and the display section 30 may be performed by either by wireless communication or wired communication. Since the display section 30 is configured similarly for both the right eye and the left eye, individual explanations thereof will be omitted. The observer OP operates the microscope 22 in order to set an observation position of the subject eye and the periphery of the subject eye as the object OB.

The optical unit 42 included in the image display device 40 is an example of an optical unit of the present disclosure, this being an optical system that functions as an objective lens to refract at least incident light from the imaging image Im and to emit the refracted light (described in detail later). Note that the optical unit 42 is an example of an optical system of the present disclosure, and has a focal point on the light incident side at a position where the imaging image (display image) Im of the object is set. Light from this focal plane (in this case, the imaging image Im or the plane where the imaging image Im is disposed) is emitted as parallel light. The optical unit 42 includes at least one doublet lens. The image display device 40 is attached to a non-illustrated stand, is independently formed from the imaging section 20, and is formed so as to be in a non-contact state with the observer OP. Forming the image display device 40 so as to be in a non-contact state with the observer OP suppresses the observer OP from feeling unsettled by contact occurring between the observer OP and the image display device 40.

In the ophthalmic system 10 according to the present exemplary embodiment, the imaging section 20, and the image display device 40, are formed independently from each other as separate units, enabling them to move separately. Thus even in cases in which the imaging section 20 has been moved to change the observation position while the observer OP is viewing the object OB (for example the subject eye and the periphery of the subject eye) using the image display device 40, the image display device 40 (for example the display section 30) does not move, and so the imaging image Im is viewable by the observer OP without head movement. This is advantageous for operation in cases such as those in which an ophthalmic surgical microscope is applied as the imaging section 20. For example, in cases in which operating is being performed while moving the operating field, the observer OP such as a doctor is able to concentrate on operating while viewing the operating field without changing viewing position. Moreover, due to being able to form the imaging section 20 and the image display device 40 independently from each other, as long as the imaging section 20 is able to image the object OB, the degrees of freedom for the shape of the imaging section itself are increased.

Note that the ophthalmic system 10 according to the present exemplary embodiment is capable of suppressing an unnatural posture of the observer OP when viewing the image display device 40. For example, the observer OP is able to observe from an optimal position, regardless of the height of the observer OP.

Moreover, the ophthalmic system 10 according to the present exemplary embodiment is able to function effectively in cases in which plural observers OP, such as a surgeon and an assistant, view the object OB (for example the subject eye and the periphery of the subject eye). Namely, the ophthalmic system 10 according to the present exemplary embodiment is provided with at least plural of the image display devices 40, with the imaging section 20 and each of the plural image display devices 40 being formed as separate units independent to each other. The ophthalmic system 10 is able to function effectively in cases in which each of the observers OP view the same imaging image or respective imaging images of the object OB using the respective image display devices 40. For example, conceivably a surgeon and an assistant view the same site on the object OB when in a state sitting on a chair or the like (in a seated state), with the surgeon taking the lead with respect to identifying and moving the viewed site on the object OB. However, were the ophthalmic system 10 to be configured as a single unit, when the surgeon moves the microscope or the like when identifying and moving the viewed site, the assistant would also need to move accompanying the movements by the surgeon. For example, in cases in which the surgeon observing the object OB moves the microscope or the like in the X direction (a direction away from the object OB), such an unexpected movement may cause an eyepiece to make contact by hitting the assistant. However, in the ophthalmic system 10 according to the present exemplary embodiment, the imaging section 20 and the image display device 40 are formed as separate units independent to each other, and are capable of moving independently of each other. The surgeon is accordingly able to concentrate on operating and the assistant to concentrate on observation, without worrying about unexpected movement of the ophthalmic system 10.

Figure 24:
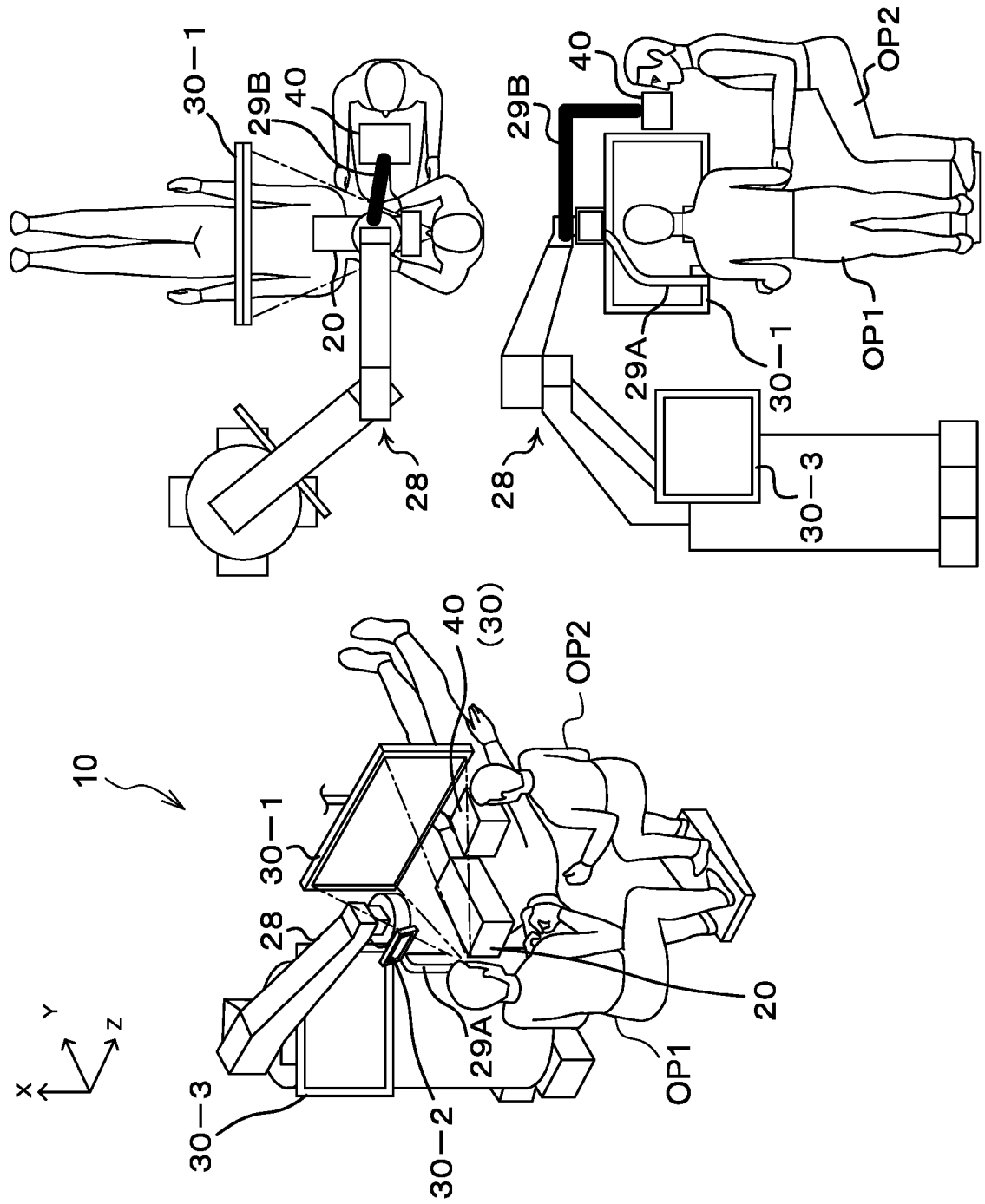
FIG. 24 is a sketch illustrating an example of an ophthalmic system according to an exemplary embodiment.

FIG. 24 illustrates an example of a configuration of an ophthalmic system equipped with the image display device according to the present exemplary embodiment.

In the example of the ophthalmic system 10 illustrated in FIG. 24, a display image of the object OB (for example the subject eye and the periphery of the subject eye) imaged by the imaging section 20 is displayed on a 3D display device 30-1, serving as a display, for the observer OP (a surgeon OP1 acting as a first user) viewing the display image while operating in a seated state. The 3D display device 30-1 is configured to employ a right-eye image (right-eye display image) and a left-eye image (left-eye display image) of the object OB having parallax as imaged by the imaging section 20 for display as a display image to present a 3D image to the surgeon OP1. Note that the present disclosure is not limited to 3D display, and the image of the object OB imaged by the imaging section 20 may be displayed while still a 2D image. Moreover, a display image the same as the display image viewed by the surgeon OP1 is displayed on the display section 30 attached to the image display device 40 for another observer OP (in this case an assistant OP2 acting as a second user) also viewing in a seated state.

The imaging section 20 is arranged on an arm 29A attached to a base 28, and is able to move as manipulated by the surgeon OP1. The 3D display device 30-1 is installed in front of (Y direction in FIG. 24) the surgeon OP1 and is adjustable in position. The image display device 40 is installed on an installation section 29B attached to the base 28 so as to be capable of moving accompanying movement of the head of the assistant OP2, and is able to move as manipulated by the assistant OP2 in any of an upward, downward, left, right, forward, or backward direction. The imaging section 20 and the image display device 40 are capable of moving independently of one another. The arm 29A is an example of an arm of the present disclosure, the installation section 29B is an example of an installation section of the present disclosure, and the base 28 is an example of a base part for attachment of the arm 29A and the installation section 29B. The example illustrated in FIG. 24 is an example in which the arm 29A and the installation section 29B are attached to the base 28; however, the arm 29A and the installation section 29B may be configured so as to be independently mounted to the ground such as the floor.

In the example illustrated in FIG. 24, other than the 3D display device 30-1 there are also displays 30-2, 30-3 installed to the base 28. The displays 30-2, 30-3 are capable of displaying the same display image as the display image viewed by the surgeon OP1. For example, the display image to present to the surgeon OP1 as a 3D image may be converted into a 2D image (for example a right-eye image or a left-eye image) and displayed on the display 30-2, or a portion of the image being displayed on the 3D display device 30-1 may be enlarged for display on the display 30-2. The display image to present to the assistant OP2 as a 3D image may also be displayed on the display 30-3. Moreover, a display image for presentation to the surgeon OP1 or the assistant OP2 may also be displayed on the display 30-3 for another observer OP (in this case a visitor OP3 as a third user).

In the ophthalmic system 10 configured in this manner, the imaging section 20 and the image display device 40 are formed independently as separate units and are also capable of moving independently. This enables the surgeon to concentrate on operating and the assistant to concentrate on observation.

Note that the 3D display device 30-1 may also be installed via the base 28. In the example illustrated in FIG. 24 the display image is displayed for the surgeon OP1 using the 3D display device 30-1, and the display image is displayed for the assistant OP2 using the image display device 40. However, the reverse is also possible.

The positions of the surgeon OP1 and the assistant OP2 are not limited to the positions illustrated in FIG. 24. For example, in cases in which operating is performed at a site on the side of the head of a patient while the patient is lying face-up (for example an ear-side incision) serving as the object OB, the surgeon OP1 may be at the position occupied by the assistant OP2 in FIG. 24, and the assistant OP2 may be at the position occupied by the surgeon OP1 in FIG. 24. In such cases, the surgeon OP1 may view the 3D display device 30-1 adjusted in position so as to be in front of the surgeon OP1 (in the opposite direction to the Z direction in FIG. 24), or may view the display 30-3. Moreover, since the image display device 40 for image display to the assistant OP2 is moveable under operation by the assistant OP2, the assistant OP2 may move the image display device 40 so as to enable the assistant OP2 to view the image at the position occupied by the surgeon OP1 in FIG. 24.

Moreover, there is no limitation to there being two observers, namely the surgeon OP1 and the assistant OP2, as the observers OP viewing images on the ophthalmic system 10. For example, three or more observers may be present. For example, consider a situation in which operating is performed by three people, these being one surgeon OP1 and two assistants OP2. In such cases, for example, conceivably the surgeon OP1 may operate at the position of the surgeon OP1 in FIG. 24, and the two assistants OP2 may assist from positions on either side of the surgeon OP1. In such cases, the surgeon OP1 might operate while viewing the 3D display device 30-1 configuring a monitor directly ahead of the surgeon OP1, the assistant in the position of the assistant OP2 in FIG. 24 might view the display 30-3 or view the image display device 40, and the assistant at a position on the opposite side to the position of the assistant OP2 in FIG. 24 might view the image display device 40.

Figure 25:
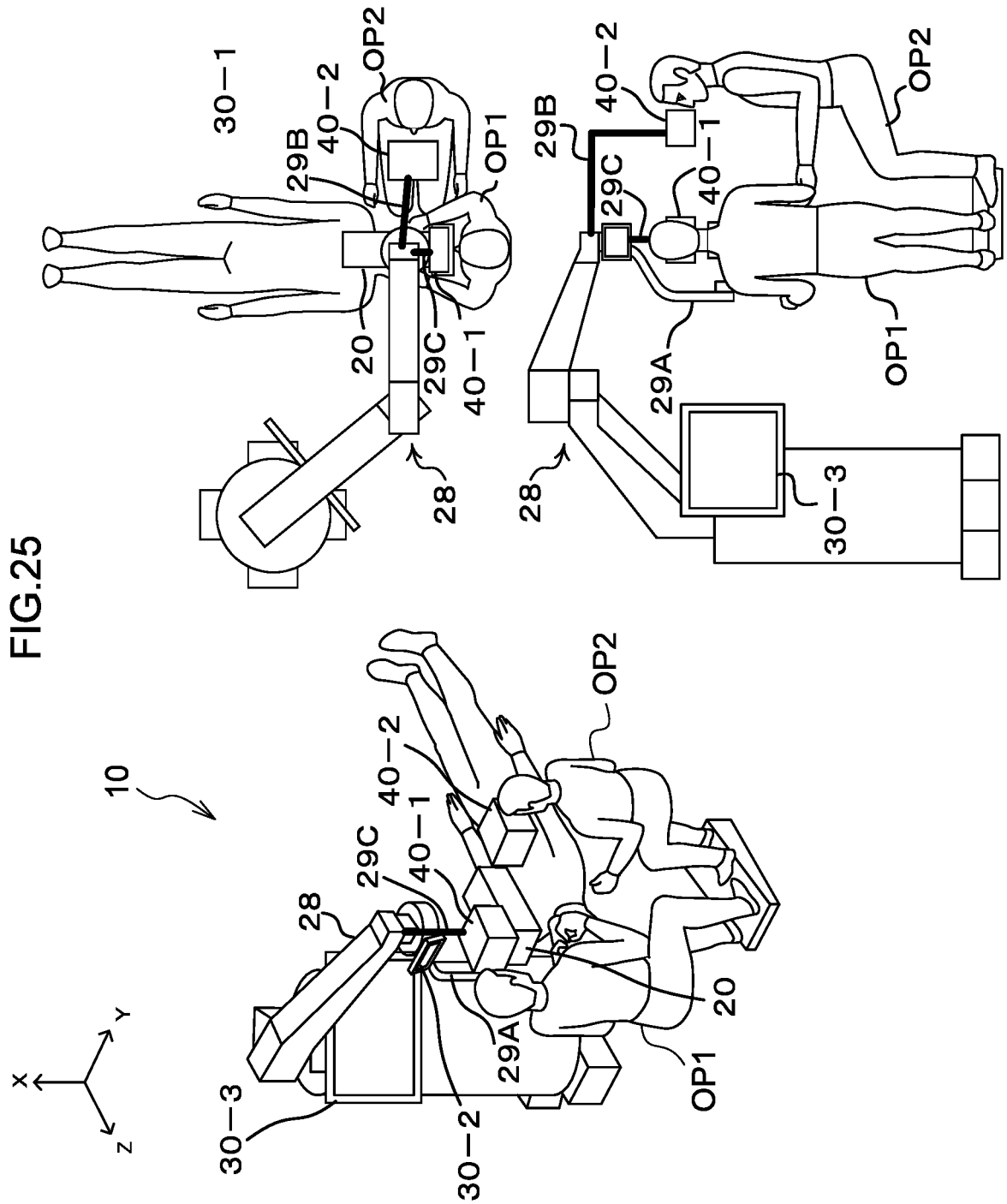
FIG. 25 is a sketch illustrating an example of an ophthalmic system according to an exemplary embodiment.

FIG. 25 illustrates another example of a configuration of an ophthalmic system equipped with the image display device according to the present exemplary embodiment.

In the example illustrated in FIG. 25, the ophthalmic system 10 includes plural image display devices 40-1, 40-2. The image display device 40-1 displays a display image for the surgeon OP1 and the image display device 40-2 displays a display image for the assistant OP2. The imaging section 20 is arranged on the arm 29A attached to the base 28, and is moveable under operation by the surgeon OP1. In the example illustrated in FIG. 25, the image display devices 40-1, 40-2 are respectively disposed for the surgeon OP1 and the assistant OP2. The image display device 40-1 is installed to the installation section 29C attached to the base 28 so as to be capable of moving accompanying movement of the head of the surgeon OP1, and is moveable under operation by the surgeon OP1 in any of an upward, downward, left, right, forward, or backward direction. The image display device 40-2 is installed to the installation section 29B attached to the base 28 so as to be capable of moving accompanying movement of the head of the assistant OP2, and is moveable under operation by the assistant OP2 in any of an upward, downward, left, right, forward, or backward direction. The imaging section 20 is accordingly capable of moving independently of the image display devices 40-1, 40-2. Moreover, the image display devices 40-1, 40-2 are capable of moving independently of each other. In this manner, the imaging section 20 and the image display devices 40 (the image display devices 40-1, 40-2 in this example) are formed independently as separate units, and are capable of moving independently, thereby enabling the surgeon to concentrate on operating and the assistant to concentrate on observation. The example illustrated in FIG. 25 is an example in which the arm 29A, the installation section 29B, and an installation section 29C are attached to the base 28; however, the arm 29A, the installation section 29B, and the installation section 29C may be configured so as to be independently mounted to the ground such as the floor.

Figure 2:
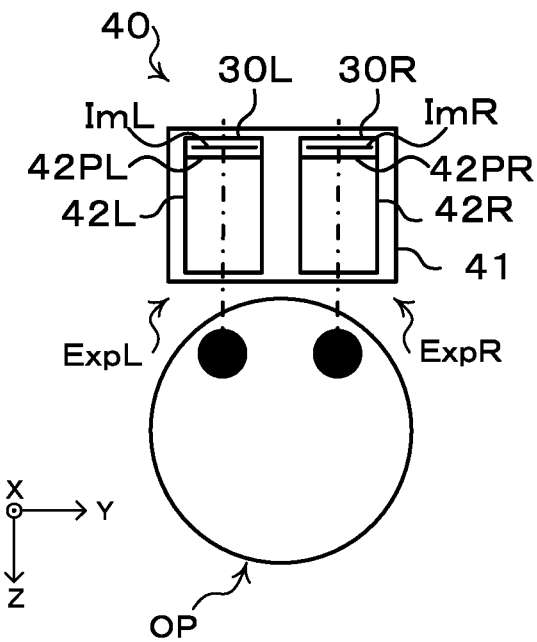
FIG. 2 is a sketch illustrating an example of a configuration of an image display device according to an exemplary embodiment.

FIG. 2 illustrates an example of a configuration of the image display device 40. Note that the image display device 40 illustrated in plan view in FIG. 2 is an example of a case in which the optical unit 42 has an independent arrangement for the right eye and for the left eye of the observer OP. The optical unit 42 includes a right-eye optical unit 42R as an example of a right side optical system, and a left-eye optical unit 42L as an example of a left side optical system. The right-eye optical unit 42R and the left-eye optical unit 42L are respectively disposed along a direction corresponding to the inter-pupil direction between the two eyes of the observer OP (for example the Y direction in FIG. 2). Note that the right-eye optical unit 42R and the left-eye optical unit 42L may be disposed along a direction corresponding to the parallax direction of parallax desired by the observer OP. For example, the right-eye optical unit 42R and the left-eye optical unit 42L may be disposed at the left and right eyes of the observer OP and spaced apart from each other along a specific direction corresponding to the inter-pupil direction of the observer OP. As viewed from the perspective of the observer OP, the right-eye optical unit 42R is disposed on the right side and the left-eye optical unit 42L is disposed on the left side. The right-eye optical unit 42R is provided with a right side attachment mechanism 42PR as an example of an attachment section to attach the right-eye display section 30R to the right-eye optical unit 42R on the light incident side of the right-eye optical unit 42R. The left-eye optical unit 42L is provided with a left side attachment mechanism 42PL as an example of an attachment section to attach the left-eye display section 30L to the left-eye optical unit 42L on the light incident side of the left-eye optical unit 42L.

As illustrated in FIG. 2, in the image display device 40, an image (a right-eye display image serving as an example of a right side display image) from the right-eye imaging section 20R, serving as an example of a right side imaging section, is formed on the display section 30R as an imaging image ImR, so as to be presented to the right eye of the observer OP through the right-eye optical unit 42R. An image (a left-eye display image serving as an example of a left side display image) from the left-eye imaging section 20L, serving as an example of a left side imaging section, is also formed on the display section 30L as an imaging image ImL, so as to be presented to the left eye of the observer OP through the left-eye optical unit 42L. The right-eye optical unit 42R and the left-eye optical unit 42L are housed in a housing case 41 that blocks external light (for example noise light) from being incident from outside the optical paths of the optical unit 42. The housing case 41 is an example of a housing section to house the right-eye optical unit 42R and the left-eye optical unit 42L and to fix them in place. The right-eye optical unit 42R and the left-eye optical unit 42L may be fixed such that their optical axes are parallel to each other. The housing case 41 may be configured from first housing cases that independently house the right-eye optical unit 42R and the left-eye optical unit 42L, and from a second housing case that houses the first housing cases.

The right-eye optical unit 42R and the left-eye optical unit 42L of the image display device 40 each include a pupil. Namely, the optical unit 42R and the left-eye optical unit 42L each form a pupil on the light exit side. Pupils may be incident pupils or exit pupils, and in the image display device 40, a right eye incident pupil InpR of the right side optical system and a left eye incident pupil InpL of the left side optical system are formed on the light exit side of the image display device 40 on optical paths outside the respective optical systems, namely are formed in front of the observer OP. In the following explanation, the right eye incident pupil InpR and the left eye incident pupil InpL are referred to collectively as the incident pupils Inp in cases in which there is no need to discriminate between left and right in the description (see FIG. 9A and FIG. 9B). Moreover, in the image display device 40, a right eye exit pupil ExpR and a left eye exit pupil ExpL are formed on the light exit side of the image display device 40 on optical paths outside the respective optical systems, namely formed in front of the observer OP. Note that in the following explanation, the right eye exit pupil ExpR and the left eye exit pupil ExpL are referred to collectively as the exit pupils Exp in cases in which there is no need to discriminate between left and right in the description (see FIG. 9A and FIG. 9B).

In the ophthalmic system 10 according to the present exemplary embodiment, each of the right-eye imaging image ImR and the left-eye imaging image ImL, which differ from each other according to parallax, are displayed in respective spaces (for example viewable areas, described later). The object OB is accordingly able to be viewed as a 3D image by the observer OP viewing with their right eye and left eye Note that the image display device 40 formed independently from the imaging section 20 and not contacting the observer OP is capable of suppressing an unsettling feeling of the observer OP caused by contact of the observer OP with the image display device 40 on moving away from the observer OP. Note that generally an imaging image Im viewable by the observer OP would become smaller as the image display device 40 and the observer OP move apart. Namely, the imaging image Im is viewable within a viewable range covering all angles of view of light exiting from the optical unit 42, known as an eyepoint. As the viewing position of the observer OP moves away from the eyepoint, light exiting from the optical unit 42 at least at some angles of view no longer reaches the observer OP. When this occurs, a state arises in which the light from the at least some of the angles of view is obstructed, with the result that the observer OP is unable to see the entire image of the object OB. Accordingly, making the eyepoint larger improves the suppression of an unsettling feeling for the observer OP caused by contact of the observer OP with the image display device 40 or contributes to enlarging an observation region where the appearance of the image does not change. The present exemplary embodiment accordingly provides the optical unit 42 that is capable of making the eyepoint larger.

Note that the light exiting from the optical unit 42 is a light beam having rotational symmetry about an axis of the optical axis of the optical unit 42. Accordingly, the eyepoint, namely the range over which the light exiting from the optical unit 42 is viewable covering all angles of view, is a substantially conical shaped region with an axis of the optical axis of the optical unit 42. In the present exemplary embodiment, the substantially conical shaped region with an axis of the optical axis of the optical unit 42 that is the range over which the light exiting from the optical unit 42 is viewable covering all angles of view, is referred to as an eyebox area. For example, the eyebox area is formed on the light exit side of the optical unit 42 (or in front of the observer OP), and is a viewable area formed by a cluster of positions where an image is viewable in a specific space. The eyebox area includes an area where the appearance of the display image (the imaging image Im in this case) does not change as long as the eyes of the observer OP are in this area when disposed in this space. In cases in which the optical unit 42 is configured by an afocal optical system, described later, the size of the image is an example of the appearance of the display image. Moreover, the eyebox area includes an area where the observable range does not change as long as the eyes are in this area when disposed in this space.

The eyebox area, which is the viewable area where the display image is viewable by the observer OP, can be derived based on the lens system included in the optical unit 42 and on the angle formed between a chief light ray at the maximum angle of view and the optical axis of the optical unit 42. Note that the chief light ray at the maximum angle of view refers to chief light ray emitted from the maximum object height of the display image, and are also chief light ray at an expected illumination angle.

Figure 3:
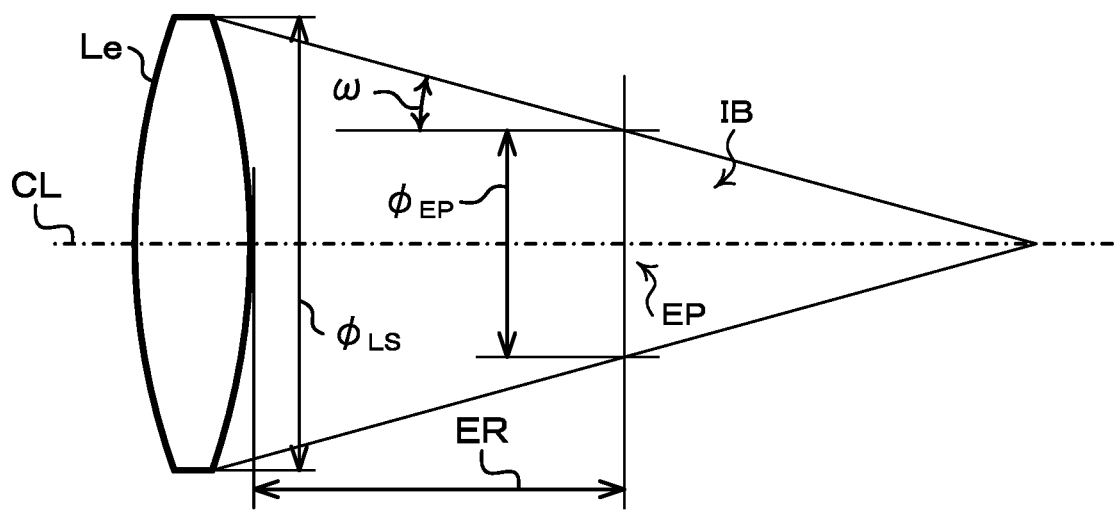
FIG. 3 is a sketch illustrating an example of a relationship between an eye of an observer and an observer-side lens of an optical unit in an ophthalmic system according to an exemplary embodiment.

FIG. 3 illustrates a relationship between a lens Le disposed on the observer side of a lens group of the optical unit 42 and an eye of the observer OP.

As illustrated in FIG. 3, the eyebox area IB, which is the viewable area where the display image (hereafter referred to as the eyebox area) is viewable by the observer OP, can be expressed by the following Equation:

$$IB=\{(\phi_{EP}/2)/\tan \omega+ER\}\cdot\{(\phi_{EP}/2)+ER\cdot\tan \omega\}^2\cdot\pi\cdot(1/3)$$

wherein $\omega$ is an angle of the half angle of view (angle formed between the chief light ray of the maximum angle of view and the optical axis) (also sometimes referred to as the angle of view hereafter), ER is the eye relief, and $\phi_{EP}$ is the eyepoint diameter.

The half angle of view $\omega$ is the angle formed between a light ray reaching the eye of the observer OP through the lens Le of the optical unit 42 closest to the eye of the observer OP in the lens group of the optical unit 42 (for example, a lens positioned at an outermost surface on the light exit side of the optical unit 42) and the optical axis CL. The eye relief ER is the distance from an apex of the lens Le to an apex of the eye of an anticipated observer OP (eyepoint). The eyepoint diameter $\phi_{EP}$ is a length, when the observer OP moves their eye along one direction (for example up and down) at the position of the eye relief ER, of a region within which light rays at all angles exiting from the lens Le arrive at the eye of the observer OP.

The eyebox area IB can be expressed by the following Equation:

$$IB=(\pi/3)\cdot(\phi_{LS}/2)^2\cdot\{(\phi_{LS}/2)/\tan \omega\}$$

wherein $\phi_{LS}$ is the effective diameter of the lens Le of the optical unit 42 closest to the eye of the observer OP Explanation follows regarding the eyebox area IB dependency on the effective diameter $\phi_{LS}$ of the lens on the observer OP eye side from out of the lens group of the optical unit 42, and dependency on the half angle of view $\omega$ of light exiting from the optical unit 42.

Figure 4:
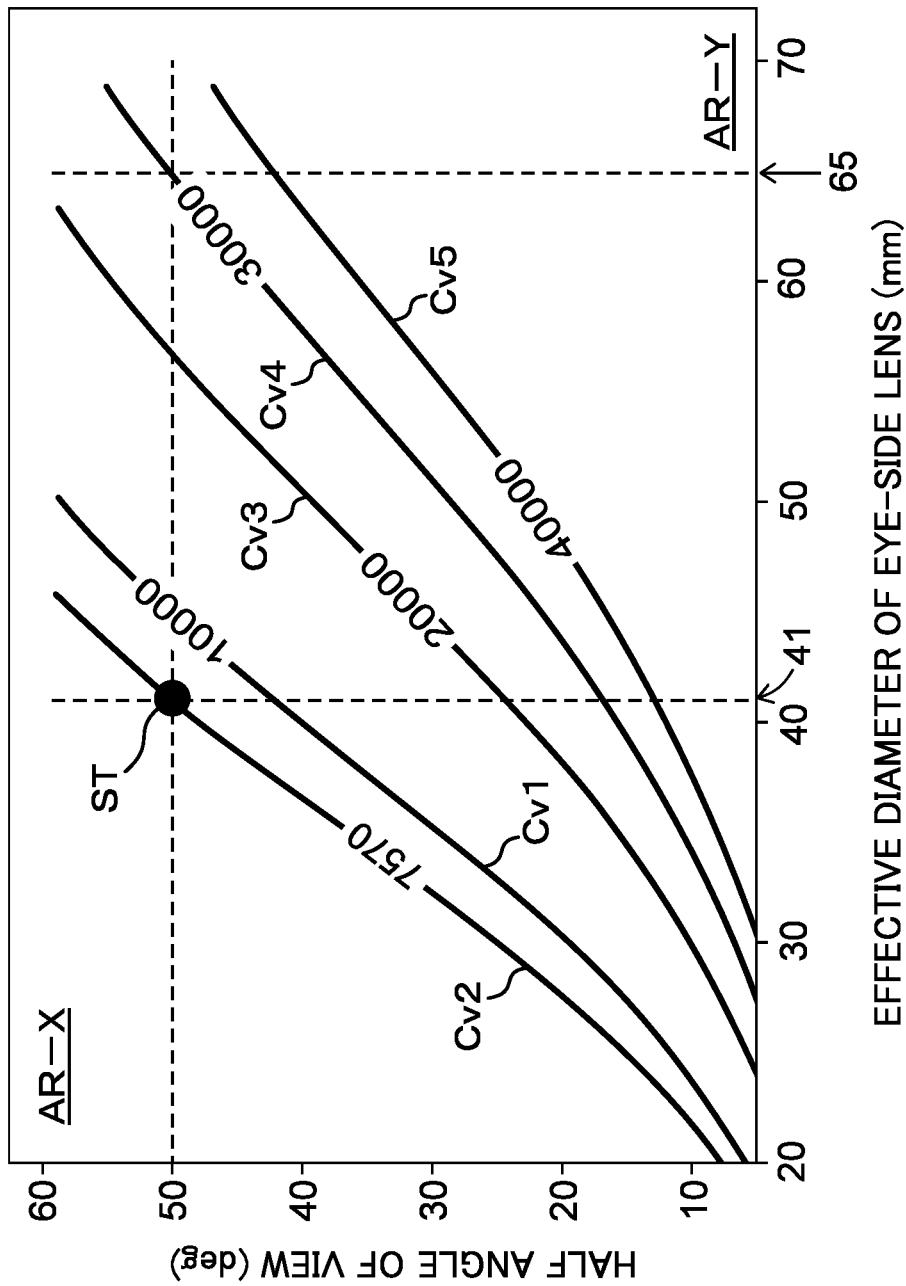
FIG. 4 is a sketch illustrating an example of relationships of eyebox area dependency on a lens of an optical unit in an ophthalmic system according to an exemplary embodiment and a half angle of view.

FIG. 4 illustrates an example of relationships of the eyebox area IB dependency on the effective diameter $\phi_{LS}$ of the lens on the observer OP eye side and on the half angle of view $\omega$ of light exiting from the optical unit 42. In FIG. 4, the half angle of view ($\omega$), as indicated by the angle formed between the optical axis CL of the optical unit 42 and the light exiting from the optical unit 42, is employed as the angle of view $\omega$.

As illustrated in FIG. 4, for example, in order to obtain an eyebox area IB of 10000 mm³ or greater, the optical unit 42 may be formed so as to satisfy a relationship between the effective diameter $\phi_{LS}$ and the half angle of view $\omega$ that gives an eyebox area IB of 10000 mm³ or greater and has a boundary of the curve Cv1 illustrated in FIG. 4 (in the example in FIG. 4, this is any relationship that falls within the area AR-Y representing a region to the right side of the drawing from the boundary of the curve Cv1). On the other hand, in the example illustrated in FIG. 4, in the optical unit 42 an eyebox area IB of 10000 mm³ or greater is difficult to obtain for relationships that fall within the area AR-X representing a region to the left side of the drawing from the boundary of the curve Cv1. Moreover, in order to obtain an eyebox area IB of 20000 mm³ or greater, for example, the optical unit 42 may be formed so as to satisfy a relationship between the effective diameter $\phi_{LS}$ and the half angle of view $\omega$ that gives an eyebox area IB of 20000 mm³ or greater and has a boundary of the curve Cv3 in FIG. 4 (in the example in FIG. 4, this is any relationship that falls within the area AR-Y representing a region to the right side of the drawing from the boundary of the curve Cv3). Similarly, in order to obtain an eyebox area IB of 30000 mm³ or greater, for example, the optical unit 42 should be formed so as to satisfy a relationship between the effective diameter $\phi_{LS}$ and the half angle of view $\omega$ that gives an eyebox area IB of 30000 mm³ or greater and has a boundary of the curve Cv4 in FIG. 4 (in the example in FIG. 4, this is any relationship that falls within the area AR-Y representing a region to the right side of the drawing from the boundary of the curve Cv4). In order to obtain an eyebox area IB of 40000 mm³ or greater, for example, the optical unit 42 should be formed so as to satisfy a relationship between the effective diameter $\phi_{LS}$ and the half angle of view $\omega$ that gives an eyebox area IB of 40000 mm³ or greater and has a boundary of the curve Cv5 in FIG. 4 (in the example in FIG. 4, this is any relationship that falls within the area AR-Y representing a region to the right side of the drawing from the boundary of the curve Cv5).

Next, discussion follows regarding the effective diameter $\phi_{LS}$ of the lens on the observer OP eye side and the half angle of view ω of the light exiting from the optical unit 42.

In the ophthalmic system 10 according to the present exemplary embodiment the observer OP views the object OB with binocular vision. The distance between the optical axis of the left-eye optical unit 42L and the optical axis of the right-eye optical unit 42R corresponds to a pupil distance PD between the two eyes, this being the inter-pupil distance of the observer OP. The pupil distance PD of a human has a statistical distribution over a range from 41 mm to 73 mm. Accordingly, assuming the pupil distance PD to be the center value of 57 mm and assuming a standard pupil diameter of 2 mm, then an eyepoint diameter $\phi_{EP}$ of 18 mm is able to cover substantially all pupil distances PD. Moreover, for a standard eyeball diameter of 24 mm and viewing ability over a rotation range of 30°, as long as the eyepoint diameter $\phi_{EP}$ is 30 mm the light will be incident to the eyes of substantially any observer OP. Moreover, the eye relief ER is preferably not less than 15 mm in consideration of contact of the eyelashes of the observer OP with the eye-side lens. The half angle of view of an eyepiece lens of a standard microscope is 20°. Based on the above, the effective diameter $\phi_{LS}$ of the observer OP eye side lens preferably has a minimum value of 41 mm.

When considering a case in which a field of view is a region affected in a subjective spatial coordinate system, albeit with poor information discrimination ability, then for example the half angle of view is preferably within ±500 for cases envisaging a field of view that creates a sense of immersion. A half angle of view within +500 enables full coverage of a region affected in a subjective spatial coordinate system, known as an induced field of view. Moreover, when gazing without straining of the eyeball or head, the half angle of view is preferably within ±450 for cases envisaging a region capable of effective information capture, known as a stable gaze field of view. Moreover, the half angle of view should include at least ±15° for cases envisaging a region capable of effective information capture instantaneously under ocular motion alone, known as an effective field of view. Moreover, the half angle of view should include at least ±2.5° for cases envisaging a central vision region having excellent vision function such as visual acuity, known as a discrimination field of view.

Accordingly, the half angle of view ω is preferably within +500 for cases envisaging an induced field of view, as described above.

Namely, the optical unit 42 is preferably configured such that the eyebox area IB satisfies the condition ω≤50°.

In such cases, the eyebox area IB formed by the light exiting from the optical unit 42 in which the effective diameter $\phi_{LS}$ of the observer OP eye side lens is 41 mm and the half angle of view ω is 500 is, substituting $\phi_{LS}$=41 and ω=50 into the above Equation, approximately 7570 mm³ (for example see the intersection point ST in FIG. 4). Configuring the optical unit 42 in such a manner so that the eyebox area IB is 7570 mm³ or greater enables substantially any observer OP to view a display image (for example the imaging image) using the induced field of view, and enables the image display device 40 to be formed such that the observer OP does not contact the optical unit 42. For example, as illustrated in FIG. 4, in order to obtain an eyebox area IB of 7570 mm³ or greater, the optical unit 42 should be formed with a relationship between the effective diameter $\phi_{LS}$ and the half angle of view ω that gives an eyebox area IB of 7570 mm³ or greater and has a boundary of the curve Cv2 illustrated in FIG. 4 (a relationship falling within the area AR-Y on the right side of the drawing having a boundary of the curve Cv2 in the example illustrated in FIG. 4).

Based on the above, the optical unit 42 of the present exemplary embodiment is preferably formed employing the following design conditions.

A first design condition is that the optical unit 42 (the optical unit 42R and the optical unit 42L) is configured such that the eyebox area IB satisfies a first condition equation $$IB \geq 7570 \text{ mm}^3.$$

Moreover, for example when envisaging an adult pupil distance PD, this enables the effective diameter $\phi_{LS}$ of the observer OP eye side lens for the above first design condition to be 53.5 mm or greater, and enables 7570 mm³ in the first condition equation to be replaced by 16800 mm³.

Namely, this enables the optical unit 42 to be configured such that the eyebox area IB satisfies the first condition equation enlarged to be IB≥16800 mm³.

The half angle of view is preferably set to within ±45° for cases envisaging a stable gaze field of view as described above. In such cases the eyebox area IB formed by the light exiting from the optical unit 42 with the effective diameter $\phi_{LS}$ of the observer OP eye side lens of 41 mm and the half angle of view ω of 45° is, by substituting $\phi_{LS}$=41 and ω=45 into the above Equation, approximately 9000 mm³. Configuring the optical unit 42 in this manner such that the eyebox area IB is 9000 mm³ or greater enables substantially any observer OP to view a display image (for example the imaging images) based on a stable gaze field of view, and enables the image display device 40 to be formed such that the observer OP does not contact the optical unit 42.

Based on the above, the optical unit 42 of the present exemplary embodiment is preferably formed employing the following design conditions for cases envisaging a stable gaze field of view.

A first design condition is that the optical unit 42 (the optical unit 42R and the optical unit 42L) is configured such that the eyebox area IB satisfies a first condition equation of IB≥9000 mm³.

Moreover, for example, in cases in which a stable gaze field of view and an adult pupil distance PD are envisaged, the effective diameter $\phi_{LS}$ of the observer OP eye side lens may be 53.5 mm or greater, and 9000 mm³ in the first condition equation may be replaced by 20000 mm³.

Namely, the optical unit 42 may be configured such that the eyebox area IB satisfies the enlarged first condition equation of the expression IB≥20000 mm³.

In cases in which the half angle of view ω of a general microscope is 200 or greater and the effective diameter $\phi_{LS}$ of the observer OP eye side lens is 41 mm, the eyebox area IB formed by the light exiting from the optical unit 42 is, by substituting $\phi_{LS}$=41 and ω=20 in the above Equation, approximately 24800 mm³. Configuring the optical unit 42 such that the eyebox area IB is 24800 mm³ or greater in this manner enables a field of view equivalent to the field of view of a general microscope to be secured, while also enabling substantially any observer OP to view the display image (for example the imaging image) and enabling the image display device 40 to be formed without the observer OP contacting the optical unit 42. Moreover, for cases envisaging an adult pupil distance PD such that the effective diameter $\phi_{LS}$ of the observer OP eye side lens is 53.5 mm or greater, from the above equation the eyebox area IB becomes 55000 mm³.

Accordingly, the optical unit 42 may be configured such that the eyebox area IB satisfies the further enlarged first condition equation of the expression IB≥24800 mm$^3$.

Moreover, the optical unit 42 is preferably configured such that the eyebox area IB satisfies the enlarged first condition equation of the expression IB≥55000 mm$^3$.

Discussion follows regarding the effective diameter $\phi_{LS}$ of the observer OP eye side lens with or without rotating the eyeball, with the half angle of view described above (in this case, ω=20) unchanged. Rotation of the eyeball includes a movement range of the eyeball under ocular motion.

In cases in which a rotation range of ±15° is viewable, the effective diameter $\phi_{LS}$ is 35.2 mm and the eyebox area IB is 15700 mm$^3$. Accordingly, for cases envisaging rotation of ±15°, the eyebox area IB is preferably 15700 mm$^3$ or greater in consideration of the degrees of freedom of the head of the observer OP.

Accordingly, the optical unit 42 may be configured such that the eyebox area IB satisfies the enlarged first condition equation of the expression IB≥15700 mm$^3$.

Note that in cases in which a rotation range of ±20° is viewable, the effective diameter $\phi_{LS}$ is 37.2 mm and the eyebox area IB is 18500 mm$^3$. Moreover, in cases in which a rotation range of ±30° is viewable, the effective diameter $\phi_{LS}$ is 41 mm and the eyebox area IB is 24800 mm$^3$. Accordingly, the eyebox area IB falls within the condition of being 15700 mm$^3$ or greater.

Note that for optical instruments such as a microscope for observation by the observer OP, for an envisaged field of view angle of 11° or greater and a standard pupil distance PD, the effective diameter $\phi_{LS}$ of the observer OP eye side lens is preferably permitted to be up to a size of around 65 mm. In such cases, the functionality of the image display device 40 of the present disclosure is expected to be achievable by the eyebox area IB being permitted to have a size of up to around 185000 mm$^3$.

Namely, the optical unit 42 is preferably configured such that the eyebox area IB satisfies a condition equation having a maximum value of the expression IB≤185000 mm$^3$.

Note that the statistical mean pupil distance PD is 65 mm. The effective diameter $\phi_{LS}$ of the observer OP eye side lens therefore preferably has a maximum value of 65 mm.

A second design condition is that the optical unit 42 is configured such that the effective diameter $\phi_{LS}$ of the observer OP eye side lens satisfies a second condition equation of the expression $\phi_{LS}$≤65 mm.

Moreover, as described above the effective diameter $\phi_{LS}$ of the observer OP eye side lens preferably has a minimum value of 41 mm.

A third design condition is that the optical unit 42 is configured such that the effective diameter $\phi_{LS}$ of the observer OP eye side lens satisfies a third condition equation of the expression $\phi_{LS}$≥41 mm.

Note that in cases in which the pupil distance PD or the effective diameter $\phi_{LS}$ of the lens is large, the eyebox area IB is preferably formed in a large region. In such cases, in order to obtain an eyebox area IB of 10000 mm$^3$ or greater, for example, the optical unit 42 may be formed such that the relationship between the effective diameter $\phi_{LS}$ and the half angle of view ω falls within the area AR-Y indicated by the region on the right side of the drawing and having the curve Cv1 illustrated in FIG. 4 as a boundary. Moreover, in order to obtain an eyebox area IB of 20000 mm$^3$ or greater, for example, the optical unit 42 may be formed such that the relationship between the effective diameter $\phi_{LS}$ and the half angle of view ω falls within the area AR-Y indicated by the region on the right side of the drawing and having the curve Cv3 illustrated in FIG. 4 as a boundary. Moreover, in order to obtain an eyebox area IB of 30000 mm$^3$ or greater, the optical unit 42 may be formed such that the relationship between the effective diameter $\phi_{LS}$ and the half angle of view ω falls within the area AR-Y indicated by the region on the right side of the drawing having a boundary of the curve Cv4 illustrated in FIG. 4. In order to obtain an eyebox area IB of 40000 mm$^3$ or greater, the optical unit 42 may be formed such that the relationship between the effective diameter $\phi_{LS}$ and the half angle of view ω falls within the area AR-Y indicated by the region on the right side of the drawing having a boundary of the curve Cv5 illustrated in FIG. 4.

The eyebox area IB that is the viewable area can be derived based on the effective diameter of the lenses included in the optical unit 42 (the right-eye optical unit 42R and the left-eye optical unit 42L), and the angle formed between the chief light ray at the maximum angle of view and the respective optical axes of the optical unit 42 (the right-eye optical unit 42R and the left-eye optical unit 42L). In such cases, the eyebox area IB that is the viewable area is preferably formed so as to satisfy a condition of the half angle of view ω being not greater than 50° (ω≤50°).

Figure 5:
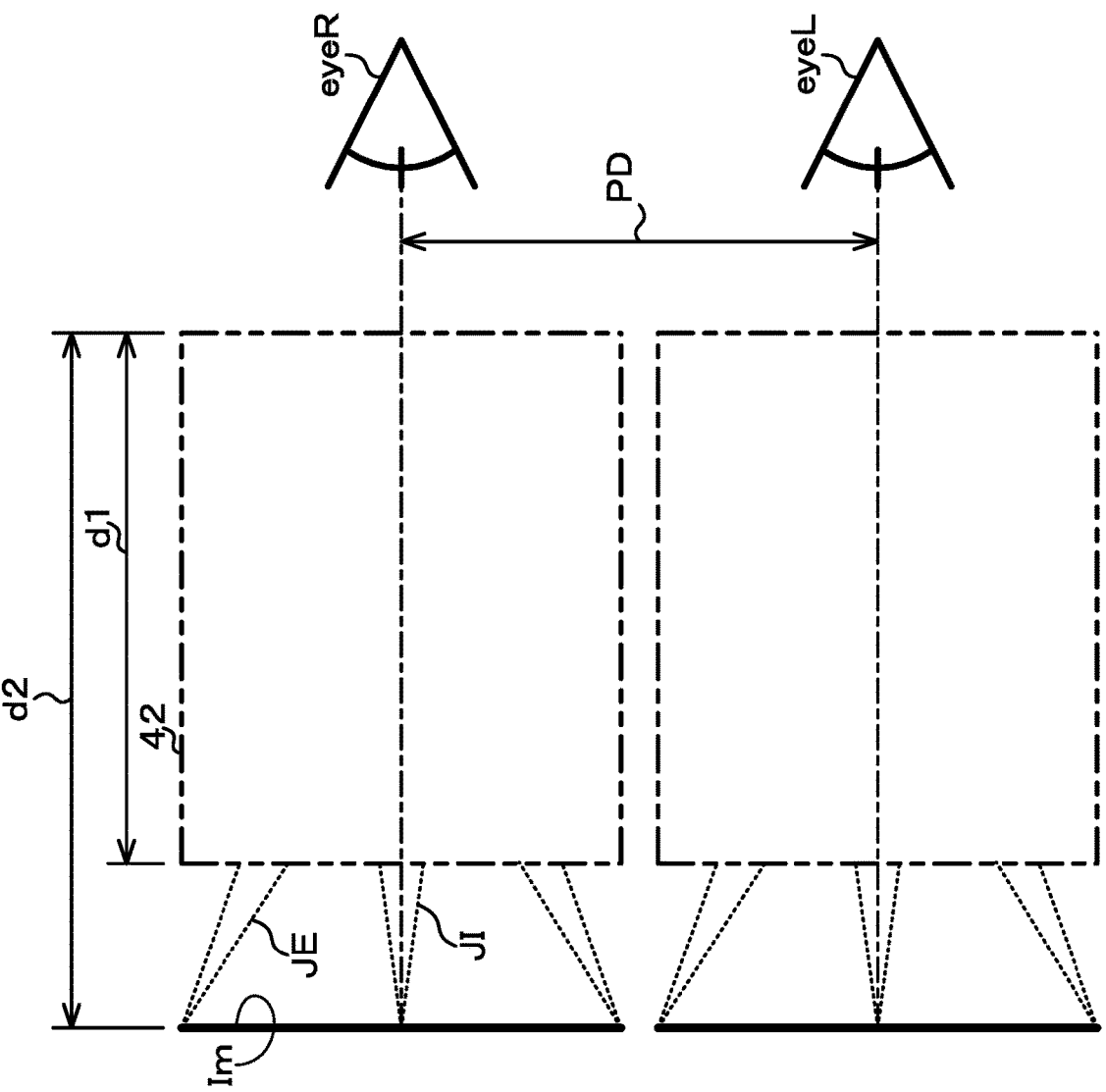
FIG. 5 is a schematic diagram illustrating a relationship between a display section and optical units in a case in which an observer views a display section with binocular vision in an ophthalmic system according to an exemplary embodiment.

FIG. 5 schematically illustrates a relationship between the display section 30 and the optical unit 42 in a case in which the display section 30 is viewed with binocular vision by the observer OP. Note that since the relationship is similar for both the optical paths of the left and right eyes, the relationship for the optical path of the right eye eyeR in FIG. 5 will be explained as an example of a right-side optical path, and explanation regarding the relationship for the optical path of the left eye eyeL as an example of a left-side optical path is omitted.

In consideration of the fact that a standard pupil distance PD, this being the inter-pupil distance of the observer OP, is from 60 mm to 70 mm, a maximum diameter of inscribed circles MD of the display section 30 corresponding to the optical paths of the left and right eyes when viewing an object with binocular vision is from 60 mm to 70 mm. Note that asymmetrical aberration not present in on-axis light is known to be present in off-axis light. However, for example, it is difficult to correct the distinctive aberration of on-axis light with the disposed lens in cases in which the lens is disposed in a region where off-axis light and on-axis light overlap. Accordingly, as illustrated in FIG. 5 of the present exemplary embodiment, such aberration can be corrected by disposing a lens of the optical unit 42 (for example the lens Lf illustrated in FIG. 9A, described later) in a region where there is a wide separation between light rays of off-axis light and on-axis light, and the off-axis light (for example a chief light rays of the off-axis light) and the on-axis light (for example chief light ray of the on-axis light) do not overlap with each other. Moreover, as illustrated in FIG. 5, on-axis light JI and off-axis light JE diverge on progression from a lens surface of the optical unit 42 toward the display section 30. In consideration of such matters, and as a result of various experiments pertaining to increasing the size of the eyebox area, the following discovery was made. This is that setting twice a distance d1 from the lens surface closest to the eye of the optical unit 42 (for example the eye-side lens surface of the lens Le illustrated in FIG. 9A, described later) to an end portion of the lens surface closest to the display section 30 (for example the display section 30-side lens surface of the lens Lf illustrated in FIG. 9A, described later) as a distance exceeding a distance d2 from the lens surface closest to the eye to the display section 30 enables aberration correction to be achieved without exacerbating aberration of on-axis light for at least one out of coma aberration, magnification related chromatic aberration, or distortion of off-axis light, even when the eyebox area is made larger in the optical unit 42.

Accordingly, a fourth design condition is, as described above, configuring the optical unit 42 so as to satisfy a fourth condition equation $$d1/d2 > 0.5$$

wherein d1 is a distance from the lens surface closest to the eye of the observer OP disposed in a space (for example within the eyebox area) to an end portion of the lens surface closest to the display section 30, and d2 is a distance from the lens surface closest to the eye of the observer OP to the display section 30.

Note that an eye relief of 20 mm is envisaged here.

Accordingly, by configuring the optical unit 42 so as to satisfy the fourth condition equation of the fourth design condition, aberration correction for coma aberration, magnification related chromatic aberration, or distortion of off-axis light is enabled without exacerbating aberration of on-axis light even in cases in which the eyebox area formed by the optical unit 42 is made larger.

An image display device according to the present exemplary embodiment includes a left-eye optical unit 42L, a right-eye optical unit 42R, and a housing case 41. The left-eye optical unit 42L is employed as a left-side optical system that includes a focal point on an incident side of light at a position for setting a left-eye display image as a display image of an object, and that is configured to emit light from a focal plane as parallel light and to form a left-eye viewable area where the left-eye display image is viewable.

The right-eye optical unit 42R is employed as a right-side optical system that includes a focal point on an incident side of light at a position for setting a right-eye display image different to the left-eye display image, and that is configured to emit light from a focal plane as parallel light and to form a right-eye viewable area where the right-eye display image is viewable. The housing section houses the left-side optical system and the right-side optical system. The optical device is configured in at least one optical system from out of the left-side optical system or the right-side optical system so as to satisfy a condition equation expressed by $$d1/d2 > 0.5$$

wherein d1 is a distance from an end portion of a lens surface on an incident side of light to an end portion of a lens surface on an exit side, and d2 is a distance from a position of the display image to the end portion of the lens surface on the light exit side.

Note that the image display device 40 of the present disclosure becomes difficult to configure if the distance d1 exceeds the distance d2, an upper limit for the value of (d1/d2) in the fourth condition equation is 1. Accordingly, the optical unit 42 is preferably configured so as to satisfy a condition equation in which an upper limit value in the fourth condition equation is expressed by $$1 > d1/d2 > 0.5$$

Note that the end portion of the lens surface serving as the origin of the distances d1, d2 will vary dependent on the shape of the lens surface. In the present exemplary embodiment, the end portion of the lens surface is a position on a flat plane orthogonal to the optical axis, that is also a flat plane contacting only an apex of the lens surface. For example, the end portion of the lens surface in the optical unit 42 closest to the display section 30 refers to a location that protrudes furthest toward the display section 30 side in the optical axis direction of the optical unit 42.

Figure 6:
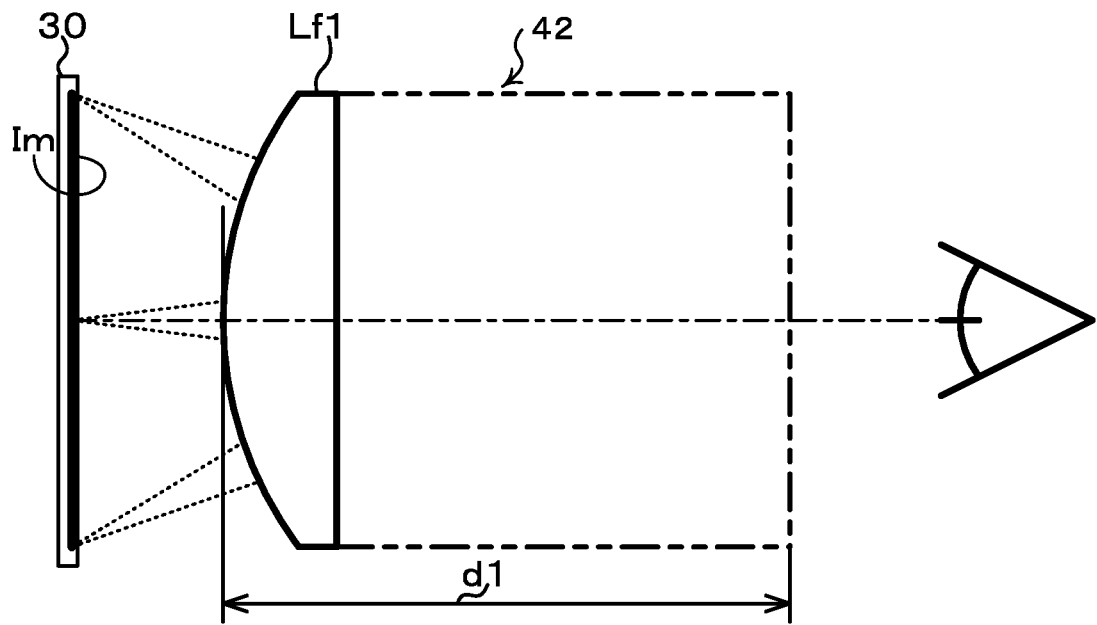
FIG. 6 is an explanatory diagram illustrating an example of an end portion of a lens surface.
Figure 7:
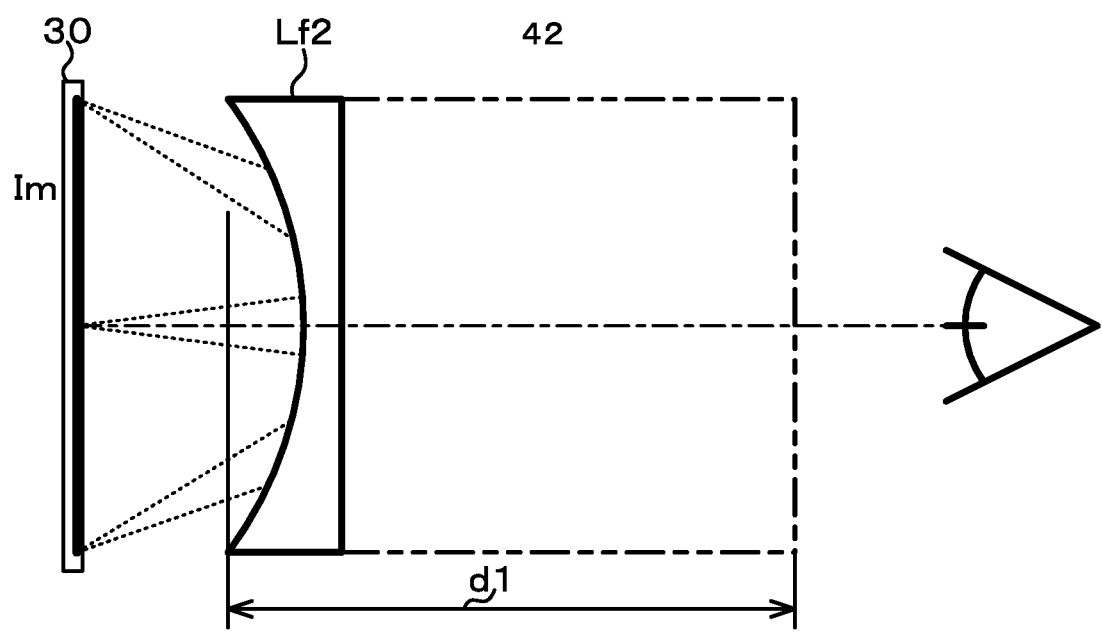
FIG. 7 is an explanatory diagram illustrating an example of an end portion of a lens surface.
Figure 8:
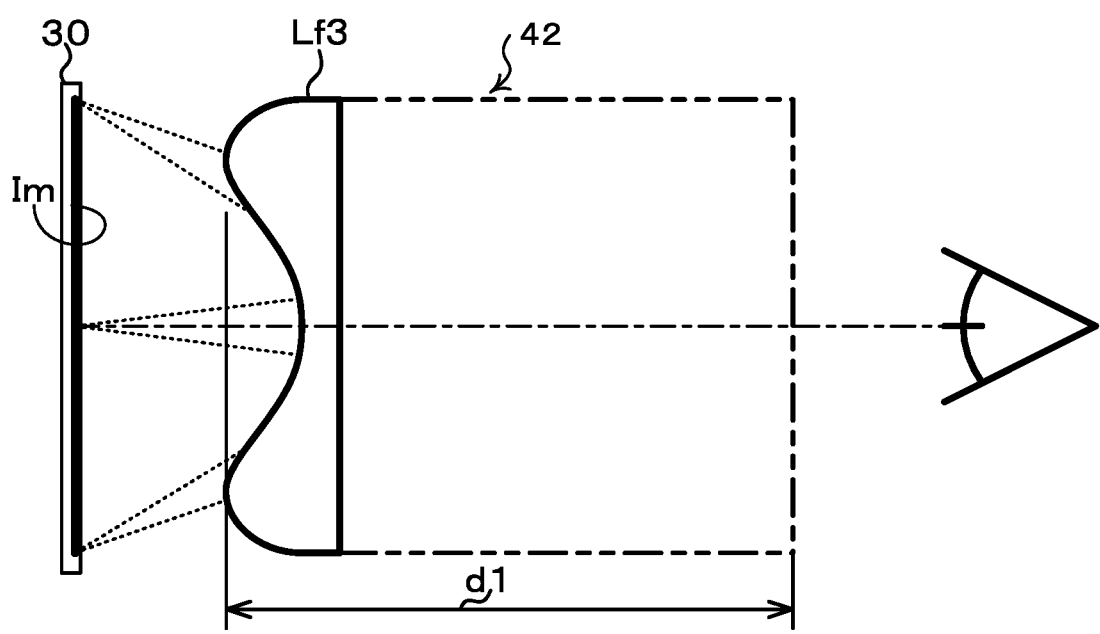
FIG. 8 is an explanatory diagram illustrating an example of an end portion of a lens surface.

FIG. 6 to FIG. 8 illustrate end portions of lens surfaces of various profiles. FIG. 6 illustrates an end portion of a lens surface of a lens Lf1 with a convex surface, FIG. 7 illustrates an end portion of a lens surface of a lens Lf2 with a concave surface, and FIG. 8 illustrates an end portion of a lens surface of a lens Lf3 with an aspherical surface. As illustrated in FIG. 6, in the case of a convex surface, the end portion is a portion where the optical axis and the position intersecting with the lens surface match, whereas as illustrated in FIG. 7, in the case of a concave surface, the end portion is an edge of the lens. As illustrated in FIG. 8, in the case of an aspherical surface, the end portion is a portion projecting further toward the display section 30 side in the optical axis direction.

In cases in which the observer OP views the imaging image Im with both eyes, as in the case of stereopsis, left and right images are preferably separated and displayed so as to correspond to the pupil distance PD between the two eyes of the observer OP. Accordingly, the lens diameters of the respective optical units 42R, 42L are preferably not greater than the pupil distance PD. For example in cases in which the pupil distance PD is set as the standard for an observer of 65 mm, the lens diameters of the respective optical units 42R, 42L are preferably not greater than 65 mm.

Accordingly, a fifth design condition and a sixth design condition as follows are preferably employed to form the optical unit 42.

The fifth design condition is that the optical unit 42 be formed with a focal length of not greater than 100 mm so as to satisfy a fifth condition equation $$f \leq (D/2)/\sin \theta$$

wherein f is the focal length of the optical unit 42, D is an imaging image Im distance as displayed by the display section 30 (for example a distance or size expressed by a diameter of an inscribed circle, a diameter of a circumscribed circle, a length of an edge, or a length of a diagonal line of an image display region), and θ is the expected illumination angle with respect to the optical axis of the optical unit 42.

The distance D of the imaging image Im is preferably set to a distance not less than the length of the shortest straight line out of straight lines on the displayed imaging image Im that pass through the center of the imaging image Im. In such cases, the distance D of the imaging image Im is the length or size of the image display region of the display section 30, and includes a distance not less than a length of a straight line passing through the center of a region (or image) in this image display region. For example, in cases in which the imaging image Im is circular in shape, then the diameter is taken as distance D. Moreover, in cases in which the imaging image Im is elliptical in shape, then the minor axis is taken as distance D. Note that the center of the imaging image Im may be the optical axis, may be a gaze axis as viewed by the observer, or may be any position within the imaging image Im.

By employing the fifth design condition, the optical unit 42 can be constructed in consideration of constraint to the size of the imaging image Im displayed by the display section 30, and in consideration of constraint to the expected illumination angle with respect to the optical axis of the optical unit 42. For example, in cases in which a distance of the imaging image Im is not greater than a standard predetermined 65 mm employed for the pupil distance PD for binocular viewing, and in which the expected illumination angle θ is equivalent to or greater than that of a standard eyepiece lens for a field number 18 at a magnification of 10×, then the focal length f is not less than 100 mm. Moreover, the expected illumination angle θ corresponds to the half angle of view ω.

A sixth design condition is that the optical unit 42 be formed with a focal length of not less than 25 mm so as satisfy a sixth conditional equation $$f \geq S/\tan R$$

wherein f is the focal length of the optical unit 42, S is the size (pixel size) of pixels configuring the imaging image Im displayed by the display section 30, and R is an eye resolving power.

By employing the sixth design condition, the optical unit 42 can be constructed considering a constraint of the size of pixels configuring the imaging image Im formed by the display section 30, and a constraint of the eye resolving power. Namely, the quality of the imaging image Im can be suppressed from being reduced to such an extent that a size of the pixels configuring the imaging image Im makes the pixels perceptible with the resolving power of the eye. For example, the focal length f is not less than 25 mm for cases in which the size of pixels configuring the imaging image Im formed by the display section 30 (pixel size) S is 15 m or greater and the eye resolving power R is 2 minutes of arc or less.

From the fifth design condition and the sixth design condition, the focal length f of the optical unit 42 is preferably from 25 mm to 100 mm for cases in which the pupil distance PD of the observer OP is 65 mm and the pixel size S for forming the imaging image Im by the display section 30 is 15 m or greater. In the image display device 40, setting the focal length f of the optical unit 42 from 25 mm to 100 mm enables image graininess resulting from being able to visually discriminate the individual pixels to be suppressed, thus improving the image quality, while maintaining the half angle of view.

As described above, cases in which a lens is disposed in a region where on-axis light JI and off-axis light JE overlap with each other (see FIG. 5) make correcting the distinctive aberration of the off-axis light JE difficult with the lens thus disposed. Accordingly, it is desirable for the chief light ray of the on-axis light JI and the chief light rays of the off-axis light JE to be separated by a larger light ray separation and the on-axis light JI (for example the chief light ray of the on-axis light) and the off-axis light JE (for example the chief light rays of the off-axis light) to be prevented from overlapping as far as possible at the lens surface on the light incident side. Namely, the optical unit 42 is preferably configured with a light ray separation such that, at the lens surface on the light incident side (for example the lens surface on the display section 30 side of the lens Lf illustrated in FIG. 9A), the chief light ray of the on-axis light and the chief light rays of the off-axis light do not overlap for light from the imaging image Im or light from the plane in which the imaging image Im is disposed.

In the optical unit 42 of the present exemplary embodiment, the lens surface at which the chief light ray are separated by the greatest amount is the lens surface closest to the display section 30, and at this lens surface (for example the lens surface on the display section 30 side of the lens Lf in FIG. 9A, described later) the chief light ray of the on-axis light JI (referred to hereafter as the chief light ray of the center angle of view) and the chief light rays of the off-axis light JE that is at the maximum angle of view at the outermost part of a displayable region of the imaging image Im (referred to hereafter as the chief light ray of the maximum angle of view) are separated from each other. Moreover, the optical unit 42 is configured such that when the chief light ray of the maximum angle of view pass through the lens surface of the optical unit 42 closest to the display section 30, the effective diameter of the lens through which these chief light ray pass is longer than a length of half the distance from the optical axis (for example the optical axis CL) to the effective diameter of the lens, and the chief light ray pass through the lens surface at a position away from the optical axis. For example, configuration is made such that for the effective diameter of the lens, the chief light ray of the maximum angle of view pass through at the outside of a concentric circular region having a diameter of half the length of the effective diameter of the lens. This is because a spherical surface or an aspherical surface is definable so as to impart the most appropriate refraction to each of the chief light ray due to there being a separation between the respective chief light ray of the on-axis light JI and the off-axis light JE at the lens surface closest to the display section 30.

As a result aberration correction is enabled to correct coma aberration, magnification related chromatic aberration, and distortion of the off-axis light without exacerbating aberration of the on-axis light, even in cases in which the eyebox area is made larger. Note that aberration correction to correct coma aberration, magnification related chromatic aberration, and distortion of the off-axis light without exacerbating aberration of the on-axis light, even in cases in which the eyebox area is made larger, is enabled by configuring the optical unit 42 to as to satisfy the fourth design condition. However, more precise aberration correction is enabled by, for the effective diameter of the lens in the optical system, configuring such that chief light ray of the maximum angle of view pass through a region further out than a concentric circular region having a diameter of half the length of the effective diameter of the lens.

Accordingly, a seventh design condition is that, for the effective diameter of the lens, the chief light ray of the maximum angle of view pass through a region further out than a concentric circular region having a diameter of half the length of the effective diameter of the lens (for example a region away from the optical axis) when the chief light ray of the maximum angle of view pass through the lens surface of the optical unit 42 located closest to the display section 30. Namely, the optical unit 42 is preferably configured such that the chief light ray of the maximum angle of view from light of the imaging image (display image) Im pass through positions at a greater diameter than half the effective diameter of the lens to which the chief light ray is incident (for example the lens Lf illustrated in FIG. 9A).

Namely, the seventh design condition is configuring the optical unit 42 so as to satisfy a seventh condition equation as expressed by a condition value Q of $$½ < Q < 1$$

$$Q = [D \cdot \{1 - (d3/P_{IN})\}]/\phi_{LF}$$

wherein D is the distance of the imaging image Im displayed by the display section 30 (for example a distance or size expressed by a diameter of an inscribed circle, a diameter of a circumscribed circle, a length of an edge, or a length of a diagonal line of an image display region), $\phi_{LF}$ is the effective diameter $\phi_{LS}$ of the lens of the optical unit 42 closest to the display section 30, d3 is the distance between the display section 30 and the lens of the optical unit 42 closest to the display section 30, and $P_{IN}$ is the distance between the display section 30 and the incident pupil Inp.

Figure 9A:
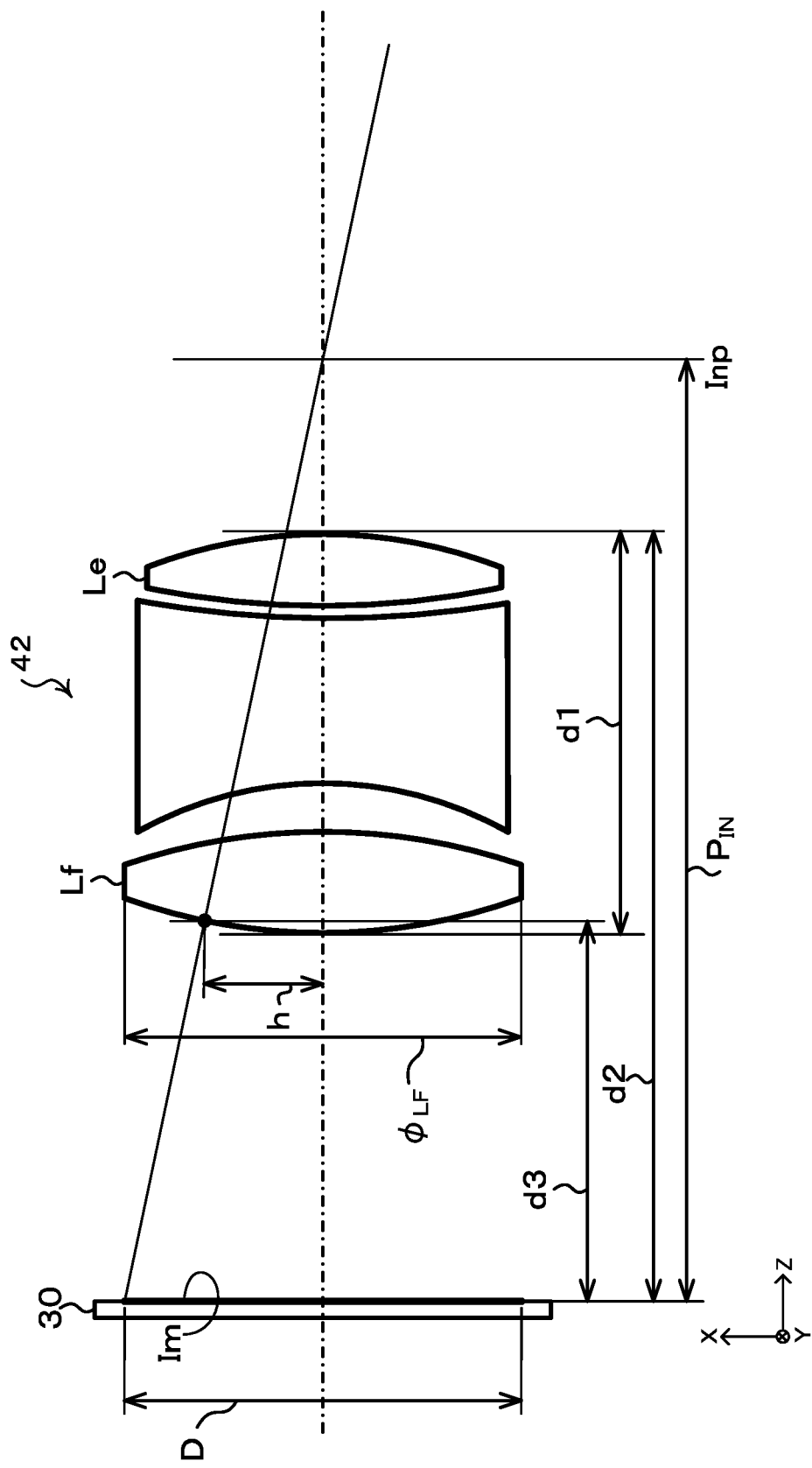
FIG. 9A is a schematic diagram illustrating a configuration of an optical unit according to an exemplary embodiment.

FIG. 9A schematically illustrates configuration of the optical unit 42. FIG. 9B illustrates an enlargement of the vicinity of the pupil. Note that due to the proximity of the incident pupil Inp and exit pupil Exp, the exit pupil Exp is not shown in FIG. 9A. Note that the positional relationship between the incident pupil Inp and the exit pupil Exp is exaggerated in FIG. 9B. The incident pupil Inp is at a position where chief light ray intersect for chief light ray at each angle of view from the imaging image Im when the chief light ray proceed in a straight line. For example, as illustrated in FIG. 9B, the position of the incident pupil Inp is at the position of intersection between a hypothetical light ray produced by extending the chief light ray at the maximum angle of view incident to the optical unit 42 in a straight line (see the light ray indicated by the dashed line in FIG. 9B) and a hypothetical light ray produced by extending the chief light ray of the center angle of view (see the light ray indicated by the single-dotted dashed line in FIG. 9B) in a straight line. On the other hand, the position of the exit pupil Exp is at a position of intersection of chief light ray when the chief light ray arriving at the imaging plane from all angles of view are projected backwards, namely a position of intersection of refracted chief light ray (see the light ray indicated by the double-dotted dashed line in FIG. 9B).

As illustrated in FIG. 9A, the chief light ray of the maximum angle of view are incident to the optical unit 42 at a slope expressed by $$(D/2)/P_{IN}$$

When this occurs, a height h from the optical axis of the lens surface of the lens Lf of the optical unit 42 closest to the display section 30 can be expressed by the following equation:

$$h = (D/2) - \{(D/2)/P_{IN}\} \cdot d3$$

$$= (D/2) \cdot \{1 - (d3/P_{IN})\}$$

Accordingly, the condition value Q can be expressed by the following equation, and the configuration of the optical unit 42 can be determined from the relationship between the effective diameter $\phi_{LF}$ of the lens of the optical unit 42 closest to the display section 30 and a height h indicating the position where the chief light ray of the maximum angle of view pass through this lens.

$$Q = h \cdot (2/\phi_{LF})$$

In the example illustrated in FIG. 9A, in the optical unit 42, the lens surface of the lens Lf on the display section 30 side is an example of a first refraction surface of the present disclosure formed by a first surface incident with light of the imaging image Im and having a convex surface toward the incident side of the light. Moreover, in the optical unit 42, the lens surface of the lens Le on the observer OP side is an example of a second refraction surface of the present disclosure formed by a second surface from which light exits and having a convex surface toward an exit side of the light. The lens surface of the lens Lf on the display section 30 side is an example of a first surface to which light to the optical unit 42 is incident, and the lens surface of the lens Le on the observer OP side is an example of a final surface from which light exits the optical unit 42. Moreover, the lens Lf is an example of a first lens of the present disclosure, and the lens Le is an example of a second lens of the present disclosure. The optical unit 42 including the lens Lf and the lens Le is an example of a lens group of the present disclosure.

Next, the design conditions described above are validated using specific examples of lenses of the optical unit 42.

Firstly, configuring the optical unit 42 so as to be capable of correcting off-axis aberration with a single lens, while also forming a large eyebox area IB, is thought of as being difficult. A configuration will now be described of an optical unit 42 formed by a single lens, for which such off-axis aberration correction is difficult.

Lens Example 1

Figure 10:
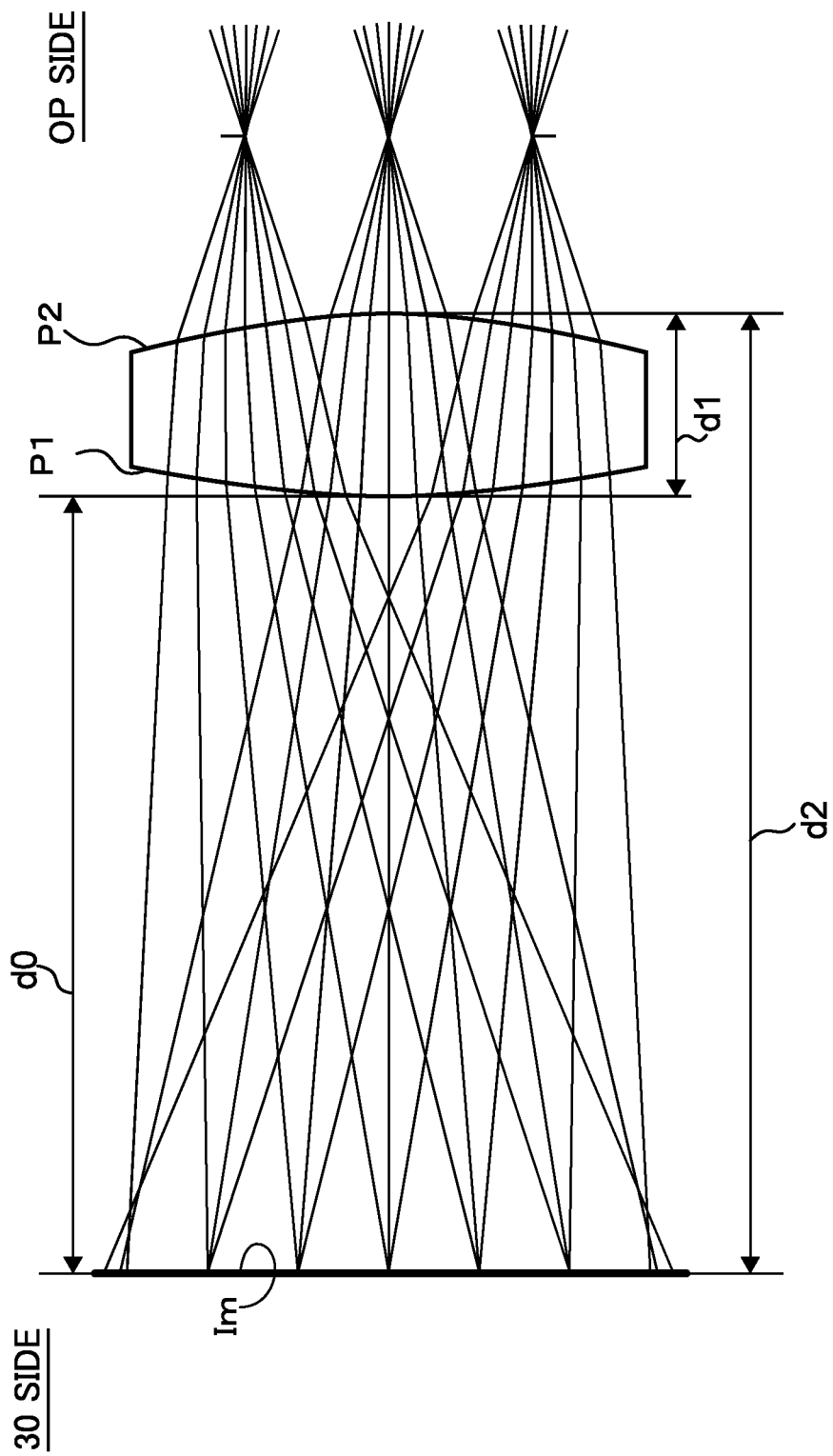
FIG. 10 is a sketch illustrating an Lens Example 1 of an optical unit.

FIG. 10 illustrates an example of a configuration of the optical unit 42 using a one-group, one-element lens as Lens Example 1, and an example of optical paths thereof. The optical unit 42R and the optical unit 42L are configured similarly to each other, and so individual description thereof will be omitted.

As illustrated in FIG. 10, the optical unit 42 is formed by a single lens including optical surfaces of Surface Nos. P1 and P2 in sequence on progression away from the imaging image Im. Each of the optical surfaces configures a refractive surface for a case in which the refractive index of a medium on one side of the optical surface of a boundary formed by the optical surface is different from the refractive index of a medium on the other side thereof. Note that the example illustrated in FIG. 10 is for a case in which the optical unit 42 is disposed with a distance of 69.7 mm as the distance d0 from the imaging image Im to an end portion of the lens surface closest to the display section 30.

Specification values of the optical unit 42 of Lens Example 1 are listed in the following Table 1.

In Table 1, Surface No. m corresponds to the Surface No. of the optical surfaces illustrated in FIG. 10. The radius of curvature r indicates a radius of curvature for each of the optical surfaces, the inter-surface distance d indicates a distance along the optical axis from each optical surface to the next optical surface, the refractive index nd indicates a refractive index with respect to D-lines, and dispersion vd indicates an Abbe number thereof. Although in the specification listed in Table 1 millimeters is adopted for the units of radius of curvature r and units of inter-surface distance d, equivalent optical properties would be obtained by proportional enlargement or proportional shrinking of the optical unit 42, and so there is no limitation to units in millimeters, and another unit may be employed.

TABLE 1

| Surface No. m | Radius of Curvature r (mm) | Inter-Surface Distance d (mm) | Refractive Index nd | Dispersion vd |
|---|---|---|---|---|
| P1 | 141.9265 | 20 | 1.62041 | 60.24 |
| P2 | 104.2765 | | | |

Note that Table 1 relates to an example in which the optical surfaces have spherical surface profiles with an axis along the optical axis CL. However, the optical surfaces are not limited to spherical surface profiles and may be aspherical surface profiles. Similar also applies to the other example lenses described later. The case envisaged here is one in which the lens effective diameter of Lens Example 1 is 24.83, and the distance of the imaging image Im (the distance or size of the image display region) is 31.66.

The optical unit 42 functions as an objective lens configuring an afocal optical system to emit light from the imaging image Im as parallel light. Namely, the optical unit 42 has a focal length f, and the display section 30 is attached to the optical unit 42 set such that the imaging image Im of the object formed by the display section 30 is positioned at the focal point on the light incident side of the optical unit 42. In this manner, the optical unit (optical system including the above lens) 42 includes a focal point on the light incident side at the position where the imaging image (display image) Im of the object is set, and emits light as parallel light from a focal plane thereof (in this case, the imaging image Im or the plane in which the imaging image Im is disposed).

As illustrated in FIG. 10, the optical unit 42 is an afocal optical system set such that the imaging image Im (display image) of the object formed by the display section 30 is positioned on the display section 30 side at the focal point position of the focal length f. Light emitted from the optical unit 42 toward the observer OP is accordingly parallel light. The parallel light emitted from the optical unit 42 reaches the eyes of the observer OP and forms an image on the retinas of the observer OP such that the imaging image Im is perceived by the observer OP.

In the optical unit 42 of Lens Example 1 illustrated in FIG. 10, the value determined by the fourth condition equation (=d1/d2) is 0.19, and the value determined by the seventh condition equation (=Q) is 0.323. The optical unit 42 of Lens Example 1 does not satisfy the fourth design condition, and although this configuration enables an increase in the size of the eyebox area formed by the optical unit 42, correction was difficult for off-axis light aberration, such as coma aberration, magnification related chromatic aberration, and distortion. Namely, aberration of the on-axis light was exacerbated by correcting aberration of the off-axis light.

Moreover, the optical unit 42 of Lens Example 1 does not satisfy the seventh design condition and there is insufficient separation between the chief light ray of the center angle of view and the chief light ray of the maximum angle of view at the lens surface of the optical unit 42 closest to the display section 30. Accordingly, defining spherical surfaces or aspherical surfaces to impart appropriate refraction for both the center angle of view and the maximum angle of view was difficult. Accordingly, were the optical unit 42 to be configured by a single lens, although increasing the size of the eyebox area is enabled, some difficult-to-correct aberration would conceivably remain and there would conceivably be a deterioration in image quality of images viewed by the observer OP.

Lens Example 2

Next, explanation follows regarding an optical unit 42 configured by a single lens and attempting to correct aberration while also forming a large eyebox area IB.

Figure 11:
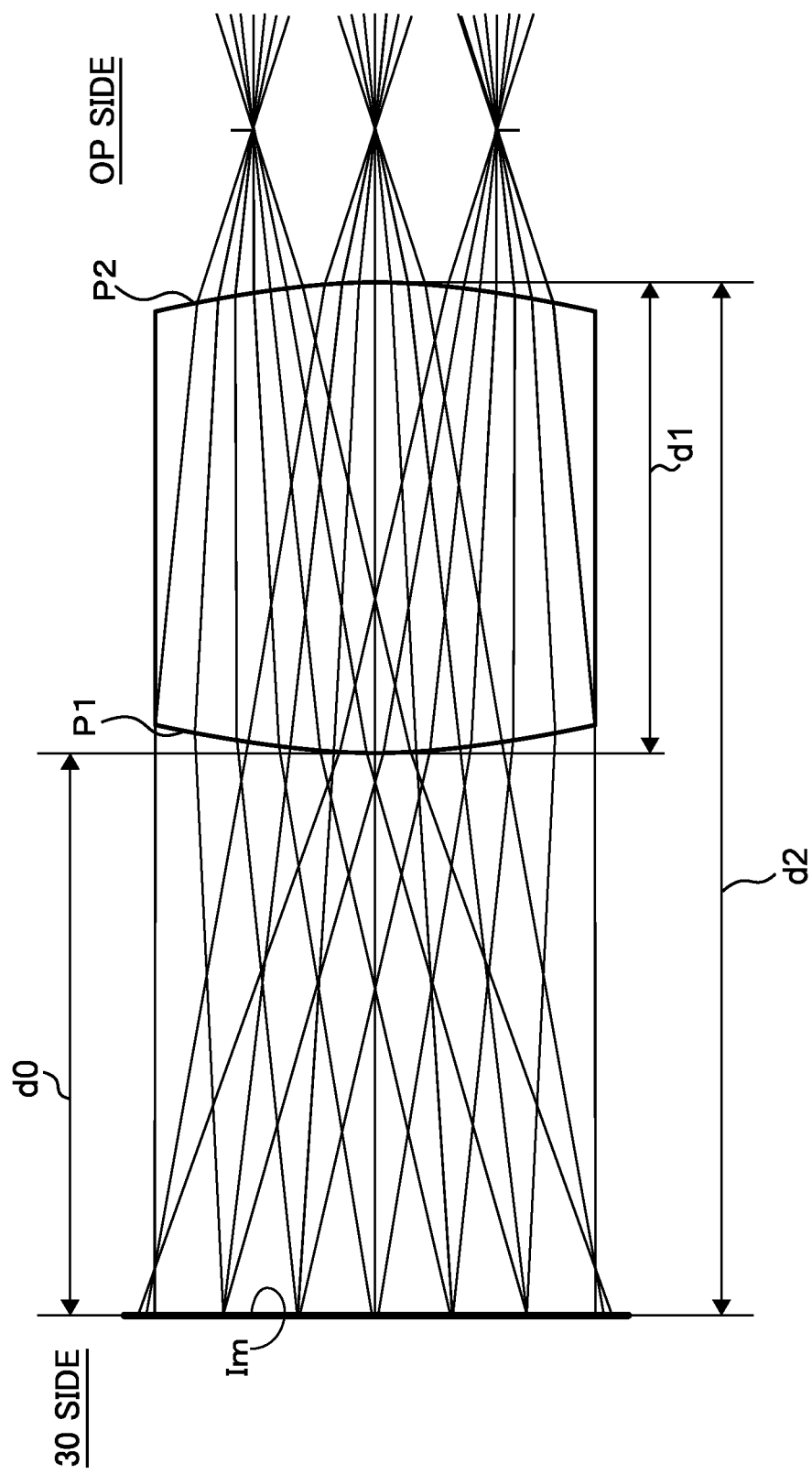
FIG. 11 is a sketch illustrating an Lens Example 2 of an optical unit.

FIG. 11 illustrates an example of a configuration of the optical unit 42 using a one-group, one-element lens having different specification values to Lens Example 1, and an example of optical paths thereof.

The optical unit 42 illustrated in FIG. 11 illustrates a case arranged with a separation of 73.76 mm as the distance d0 from the imaging image Im to an end portion of the lens surface closest to the display section 30.

Specification values of the optical unit 42 of Lens Example 2 are listed in the following Table 2.

In Table 2, Surface No. m corresponds to the Surface No. of the optical surfaces illustrated in FIG. 3. The radius of curvature r indicates a radius of curvature for each of the optical surfaces, the inter-surface distance d indicates a distance along the optical axis from each optical surface to the next optical surface, the refractive index nd indicates a refractive index with respect to D-lines, and dispersion vd indicates an Abbe number thereof. Although in the specifications listed in Table 2 millimeters is adopted for units of radius of curvature r and units of inter-surface distance d, equivalent optical properties would be obtained by proportional enlargement or proportional shrinking of the optical unit 42R, and so there is no limitation to units in millimeters, and another unit may be employed. Moreover, the case envisaged here is one in which the lens effective diameter of Lens Example 2 is 29.02, and the distance of the imaging image Im (distance or size of the image display region) is 30.99.

TABLE 2

| Surface No. m | Radius of Curvature r (mm) | Inter-Surface Distance d (mm) | Refractive Index nd | Dispersion vd |
|---|---|---|---|---|
| P1 | 111.23 | 61.62 | 1.62041 | 60.24 |
| P2 | −110.5355 | | | |

In the optical unit 42 of Lens Example 2, the value determined by the fourth condition equation (=d1/d2) is 0.455, and the value determined by the seventh condition equation (=Q) is 0.553. The optical unit 42 of Lens Example 2 satisfies the seventh design condition. Accordingly, a spherical surface or an aspherical surface is definable for the lens surface closest to the display section 30 so as to impart appropriate refraction at both the center angle of view and the maximum angle of view. However, the optical unit 42 of Lens Example 2 does not satisfy the fourth design condition. Accordingly, although an increase in the size of the eyebox area formed by the optical unit 42 is enabled, aberration correction is difficult for off-axis light, such as coma aberration, magnification related chromatic aberration, and distortion, and aberration of the on-axis light is exacerbated by correcting aberration of the off-axis light.

Accordingly, were the optical unit 42 to be configured by a single lens, although an increase in the size of the eyebox area formed by the optical unit 42 is enabled, correction is sometimes difficult of aberration such as coma aberration, magnification related chromatic aberration, and distortion of off-axis light. However, satisfying the seventh design condition conceivably enables aberration to be corrected to an extent expected to improve image quality. Namely, the Lens Example 2 enables the size of the eyebox area to be increased, and although the various aberration corrections gives rise to difficult circumstances, due to spherical surfaces or aspherical surfaces being definable so as to impart appropriate refraction for both the center angle of view and the maximum angle of view, an improvement in image quality of images viewed by the observer OP can be expected in comparison to a lens that does not satisfy the seventh design condition.

Lens Example 3

Figure 12:
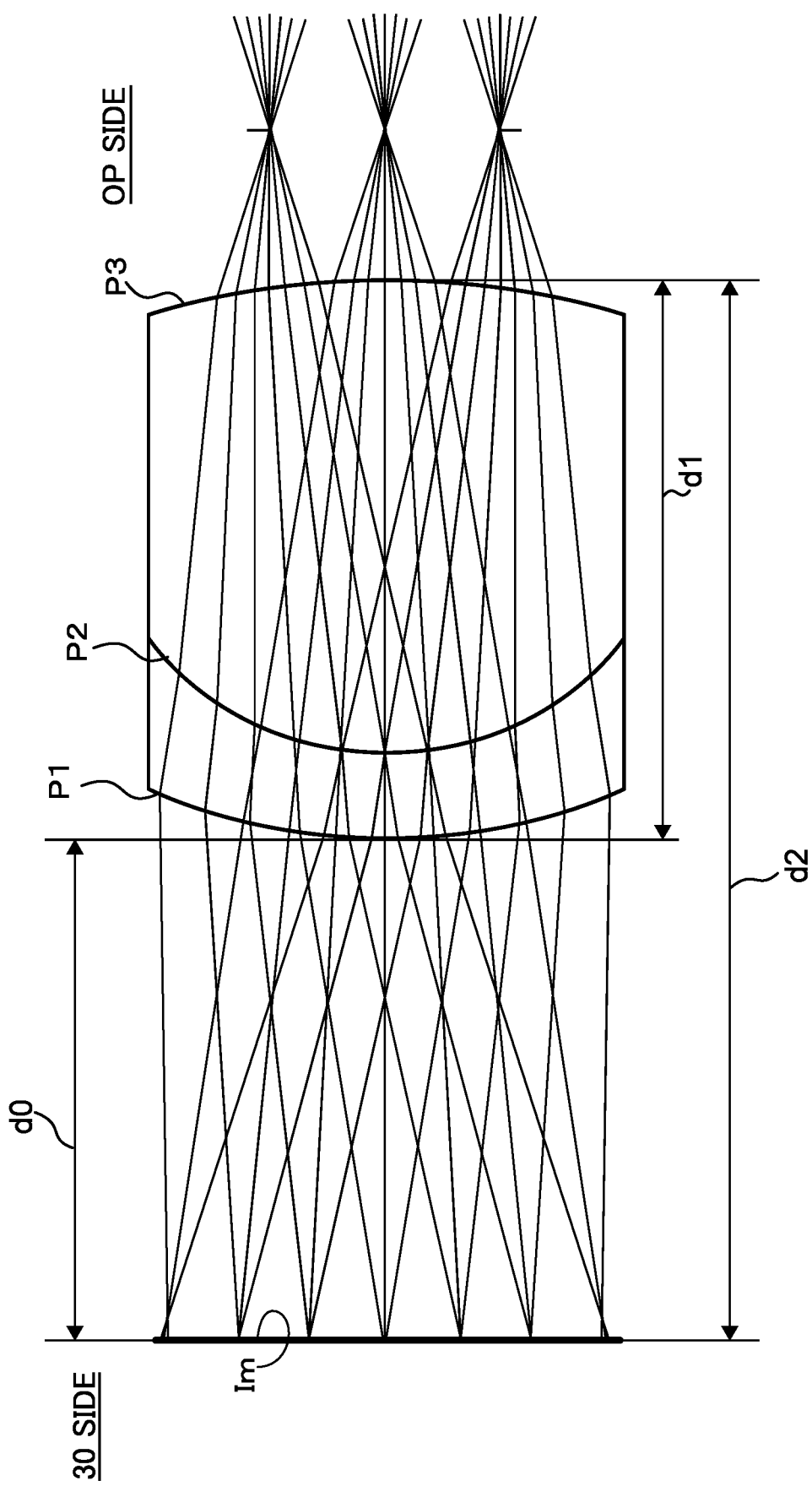
FIG. 12 is a sketch illustrating an Lens Example 3 of an optical unit.

FIG. 12 illustrates an example in which an optical unit 42 is configured by a one-group, two-element lens as Lens Example 3, and an example of optical paths thereof.

The optical unit 42 illustrated in FIG. 12 is formed by the one-group, two-element lens with optical surfaces of Surface Nos. P1, P2, P3 in sequence on progression away from the imaging image Im. In the example illustrated in FIG. 12, the optical unit 42 illustrates a case arranged with a separation of 69.7 mm as the distance d0 from the imaging image Im.

Specification values of the optical unit 42 of Lens Example 3 are listed in the following Table 3. Note that the case envisaged here is one in which the lens effective diameter of Lens Example 3 is 31.20, and the distance of the imaging image Im (distance or size of the image display region) is 31.19.

TABLE 3

| Surface No. m | Radius of Curvature r (mm) | Inter-Surface Distance d (mm) | Refractive Index nd | Dispersion vd |
|---|---|---|---|---|
| P1 | 84.1051 | 11.4 | 1.7552 | 27.57 |
| P2 | 40.2515 | 66.5 | 1.62041 | 60.24 |
| P3 | −104.34 | | | |

In the optical unit 42 of Lens Example 3, the value determined by the fourth condition equation (=d1/d2) is 0.53, and the value determined by the seventh condition equation (=Q) is 0.643. The optical unit 42 of Lens Example 3 satisfies the fourth design condition, enabling an increase in the size of the eyebox area formed by the optical unit 42, and enabling aberration correction for off-axis light, such as coma aberration, magnification related chromatic aberration, and distortion.

The optical unit 42 of Lens Example 3 also satisfies the seventh design condition, enabling separation of the chief light ray of the center angle of view and of the maximum angle of view at the lens surface of the optical unit 42 closest to the display section 30. Accordingly, a spherical surface or an aspherical is definable so as to impart appropriate refraction for both the center angle of view and the maximum angle of view. The Lens Example 3 accordingly enables the size of the eyebox area to be increased, and also enables correction of various aberrations, and can therefore be expected to improve the image quality of images viewed by the observer OP.

Note that in cases in which the optical unit 42 is formed using a one-group, two-element lens configuration, the second surface is packed from both sides with glass material. This is undesirable from the perspectives of cost and weight, and so a configuration of two or more groups is preferable.

Lens Example 4

Figure 13:
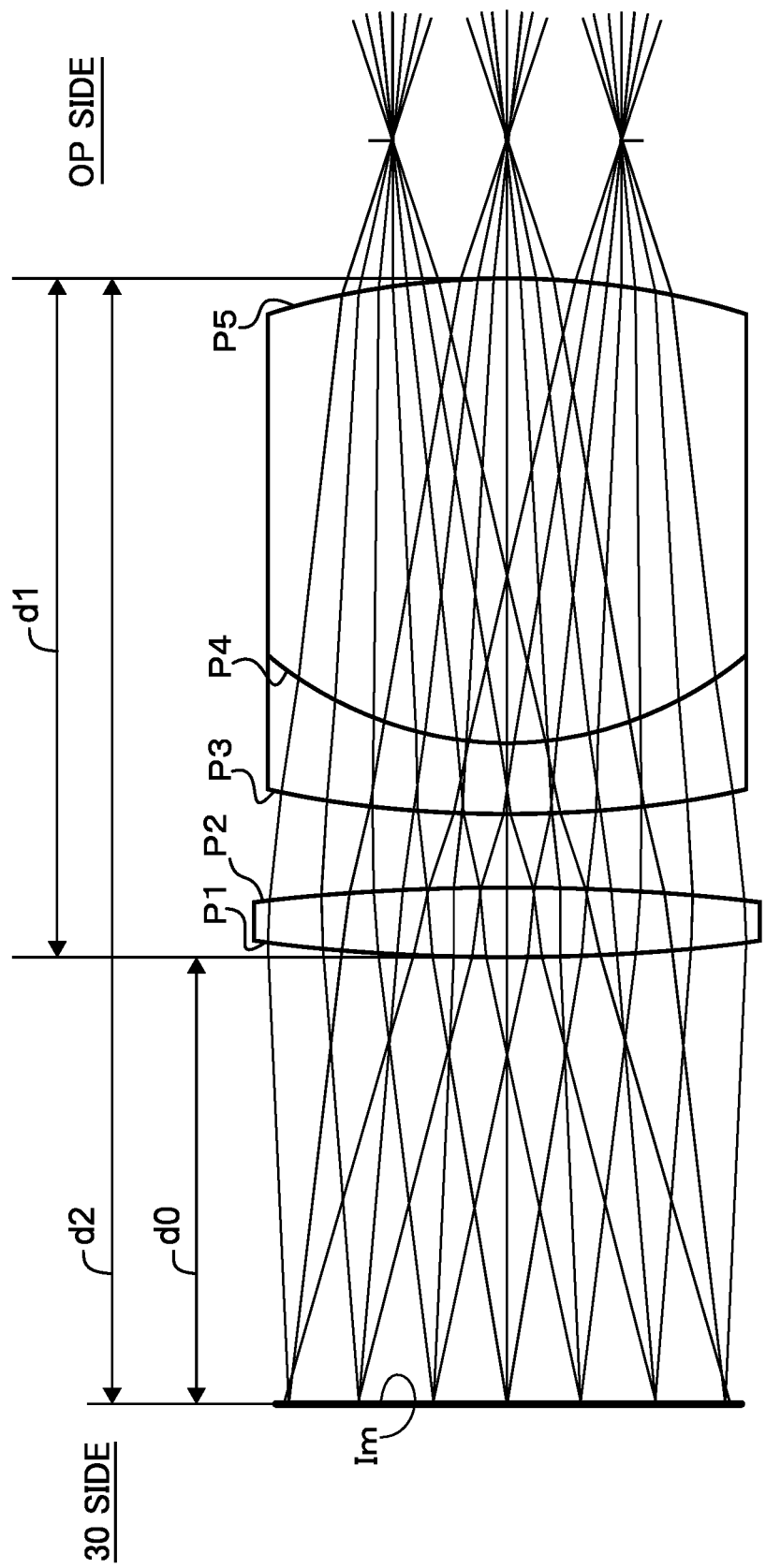
FIG. 13 is a sketch illustrating an Lens Example 4 of an optical unit.

FIG. 13 illustrates an example in which an optical unit 42 is configured by a two-group, three-element lens as Lens Example 4, and an example of optical paths thereof.

The optical unit 42 illustrated in FIG. 13 is formed by a two-group, three-element lens with optical surfaces of Surface Nos. P1, P2, P3, P4, P5 in sequence on progression away from the imaging image Im. In the example illustrated in FIG. 13, the optical unit 42 illustrates a case arranged with a separation of 62.8 mm as the distance d0 from the imaging image Im.

Specification values of the optical unit 42 of Lens Example 4 are listed in the following Table 4. Note that the case envisaged here is one in which the lens effective diameter of Lens Example 4 is 33.45, and the distance of the imaging image Im (distance or size of the image display region) is 31.26.

TABLE 4

| Surface No. m | Radius of Curvature r (mm) | Inter-Surface Distance d (mm) | Refractive Index nd | Dispersion vd |
|---|---|---|---|---|
| P1 | 276.70 | 10 | 1.62041 | 60.24 |
| P2 | −252.79 | 10 | | |
| P3 | 158.37 | 10 | 1.75520 | 27.57 |
| P4 | 50.84 | 65 | 1.62041 | 60.24 |
| P5 | −118.87 | | | |

In the optical unit 42 of Lens Example 4, the value determined by the fourth condition equation (=d1/d2) is 0.60, and the value determined by the seventh condition equation (=Q) is 0.737. The optical unit 42 of Lens Example 4 satisfies the fourth design condition, enabling an increase the size of the eyebox area formed by the optical unit 42, and also enabling aberration correction for off-axis light, such as coma aberration, magnification related chromatic aberration, and distortion. Moreover, the optical unit 42 of Lens Example 4 also satisfies the seventh design condition, enabling separation of the chief light ray of the center angle of view and of the maximum angle of view at the lens surface of the optical unit 42 closest to the display section 30. Accordingly, a spherical surface or an aspherical surface is definable so as to impart appropriate refraction for both the center angle of view and the maximum angle of view.

The Lens Example 4 accordingly enables the size of the eyebox area to be increased, and also enables correction of various aberrations, and so an improvement in the image quality of images viewed by the observer OP can be expected.

Lens Example 5

Figure 14:
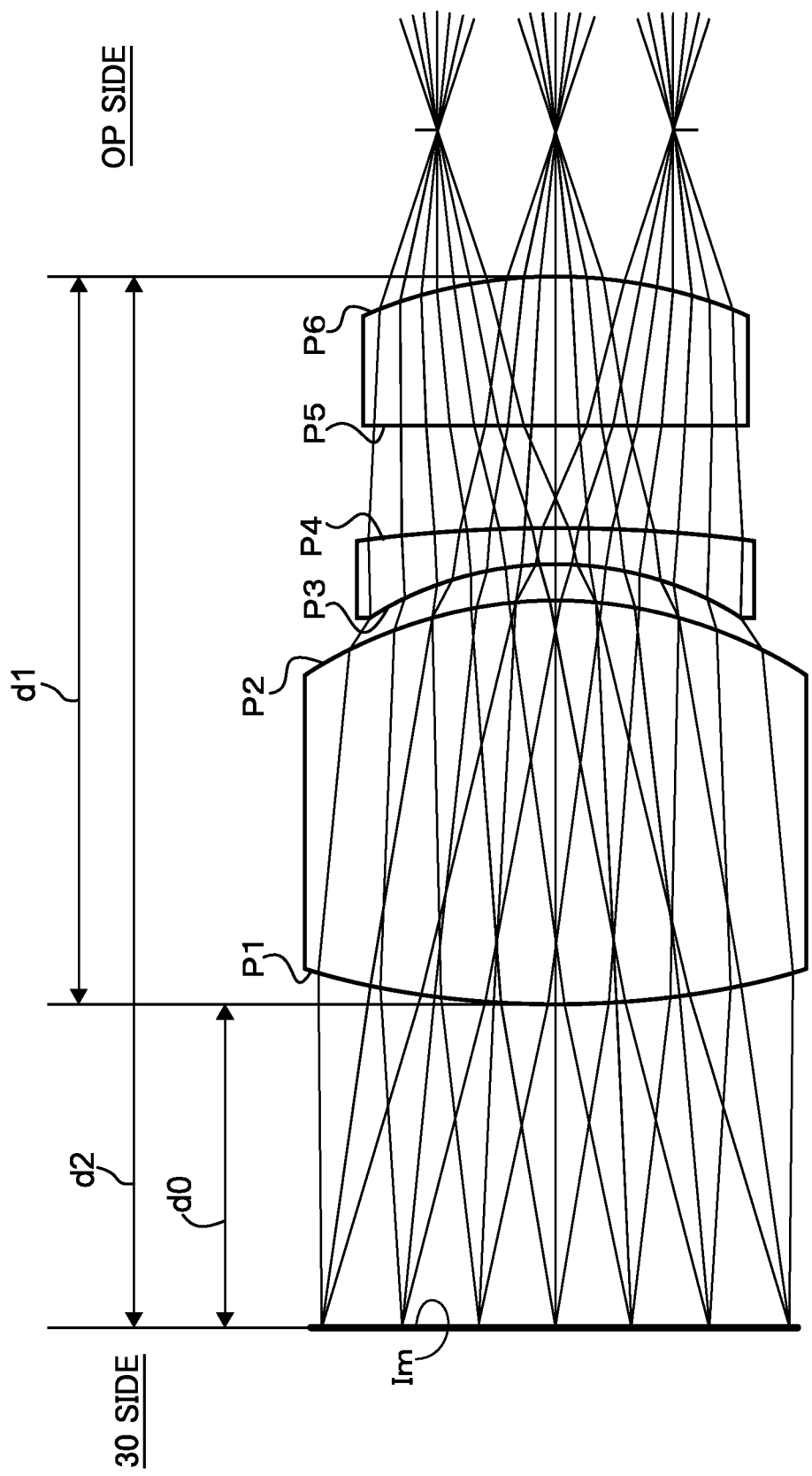
FIG. 14 is a sketch illustrating an Lens Example 5 of an optical unit.

FIG. 14 illustrates an example of a configuration of an optical unit 42 formed by a three-group, three-element lens as Lens Example 5, and an example of optical paths thereof.

The optical unit 42 illustrated in FIG. 14 is formed by the three-group, three-element lens with optical surfaces of Surface Nos. P1, P2, P3, P4, P5, P6 in sequence on progression away from the imaging image Im. In the example illustrated in FIG. 14, the optical unit 42 illustrates a case arranged with a separation of 43.8 mm as the distance d0 from the imaging image Im.

Specification values of the optical unit 42 of Lens Example 5 are listed in the following Table 5. Note that the case envisaged here is one in which the lens effective diameter of Lens Example 5 is 32.16, and the distance of the imaging image Im (distance or size of the image display region) is 31.59.

TABLE 5

| Surface No. m | Radius of Curvature r (mm) | Inter-Surface Distance d (mm) | Refractive Index nd | Dispersion vd |
|---|---|---|---|---|
| P1 | 121.02 | 55 | 1.62041 | 60.24 |
| P2 | −60.97 | 5 | | |
| P3 | −45.65 | 5 | 1.75520 | 27.57 |
| P4 | −188.15 | 14 | | |
| P5 | ∞ | 20 | 1.62041 | 60.24 |
| P6 | −67.38 | | | |

In the optical unit 42 of Lens Example 5, the value determined by the fourth condition equation (=d1/d2) is 0.69, satisfying the fourth design condition. Moreover, the value determined by the seventh condition equation (=Q) is 0.816, satisfying the seventh design condition. The optical unit 42 of Lens Example 5 accordingly enables the size of the eyebox area formed by the optical unit 42 to be increased, and also enables aberration correction for off-axis light, such as coma aberration, magnification related chromatic aberration, and distortion. Moreover, the chief light ray of the center angle of view and of the maximum angle of view can be separated at the lens surface closest to the display section 30, and a spherical surface or an aspherical surface is definable so as to independently impart appropriate refraction for both the center angle of view and the maximum angle of view.

The Lens Example 5 accordingly enables the size of the eyebox area to be increased, and also enables correction of various aberrations, and can therefore be expected to improve the image quality of images viewed by the observer OP.

Lens Example 6

Figure 15:
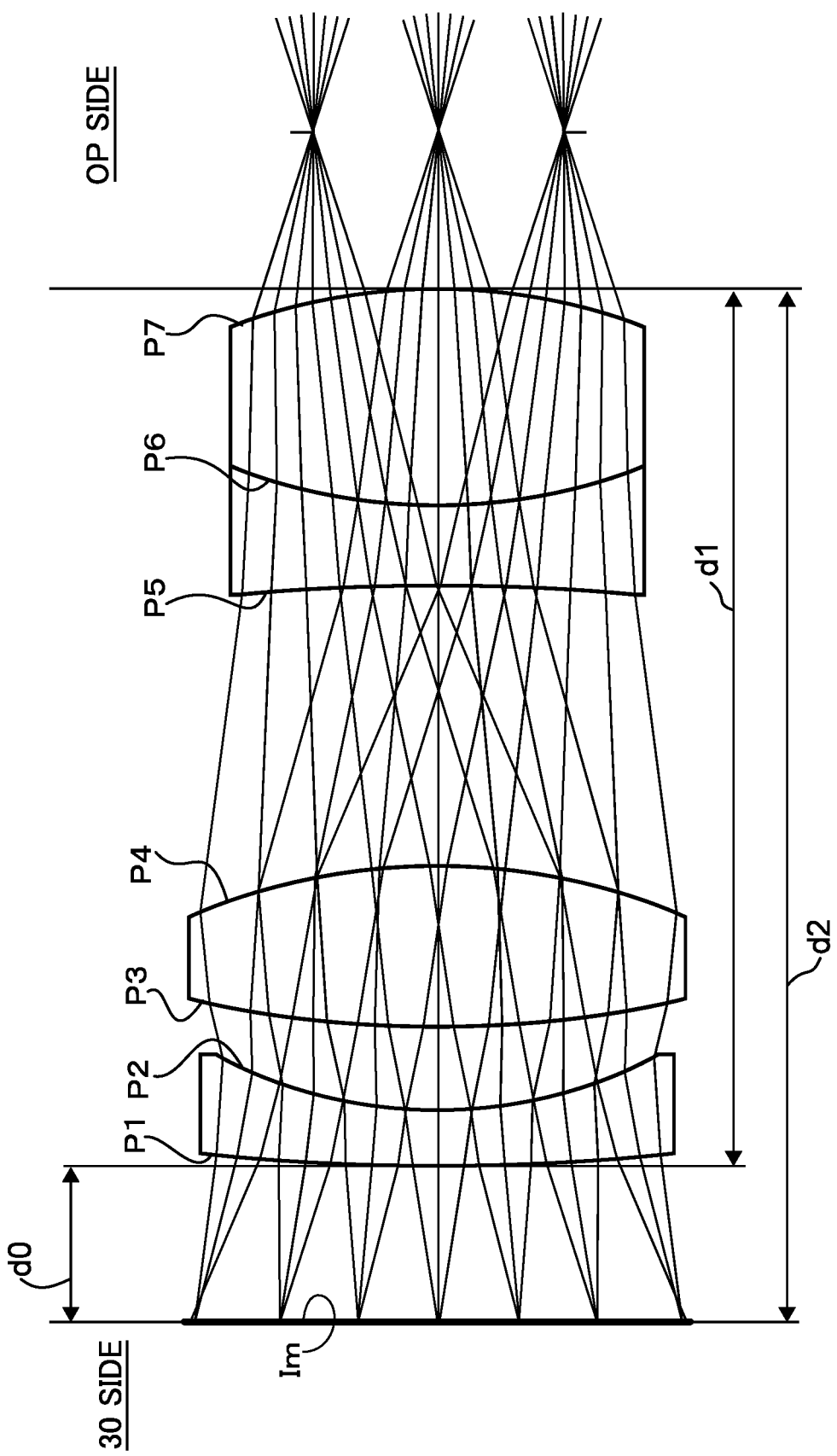
FIG. 15 is a sketch illustrating an Lens Example 6 of an optical unit.

FIG. 15 illustrates an example of a configuration of an optical unit 42 formed by a three-group, four-element lens as Lens Example 6, and an example of optical paths thereof.

The optical unit 42 illustrated in FIG. 15 is formed by the three-group, four-element lens with optical surfaces of Surface Nos. P1, P2, P3, P4, P5, P6, P7 in sequence on progression away from the imaging image Im. In the example illustrated in FIG. 15, the optical unit 42 illustrates a case arranged with a separation of 19.5 mm as the distance d0 from the imaging image Im.

Specification values of the optical unit 42 of Lens Example 6 are listed in the following Table 6. Note that the case envisaged here is one in which the lens effective diameter of Lens Example 6 is 28.38, and the distance of the imaging image Im (distance or size of the image display region) is 31.80.

TABLE 6

| Surface No. m | Radius of Curvature r (mm) | Inter-Surface Distance d (mm) | Refractive Index nd | Dispersion vd |
| --- | --- | --- | --- | --- |
| P1 | 390.308 | 6.9 | 1.80440 | 39.6 |
| P2 | 58.352 | 10.8 | | |
| P3 | 139.865 | 20.5 | 1.62041 | 60.24 |
| P4 | −80.487 | 35.5 | | |
| P5 | −408.595 | 10.4 | 1.80100 | 34.92 |
| P6 | 70.045 | 27.67 | 1.6968 | 55.52 |
| P7 | −70.045 | | | |

In the optical unit 42 of Lens Example 6, the value determined by the fourth condition equation (=d1/d2) is 0.85, satisfying the fourth design condition. Moreover, the value determined by the seventh condition equation (=Q) is 0.80, satisfying the seventh design condition. The optical unit 42 of Lens Example 6 accordingly enables the size of the eyebox area formed by the optical unit 42 to be increased, and also enables aberration correction for off-axis light, such as coma aberration, magnification related chromatic aberration, and distortion. Moreover, the chief light ray of the center angle of view and of the maximum angle of view can be separated at the lens surface closest to the display section 30, and a spherical surface or an aspherical surface is definable so as to independently so as to impart appropriate refraction for both the center angle of view and the maximum angle of view.

The Lens Example 6 accordingly enables the size of the eyebox area to be increased, and also enables correction of various aberrations, and can therefore be expected to improve the image quality of images viewed by the observer OP.

Lens Example 7

Figure 16:
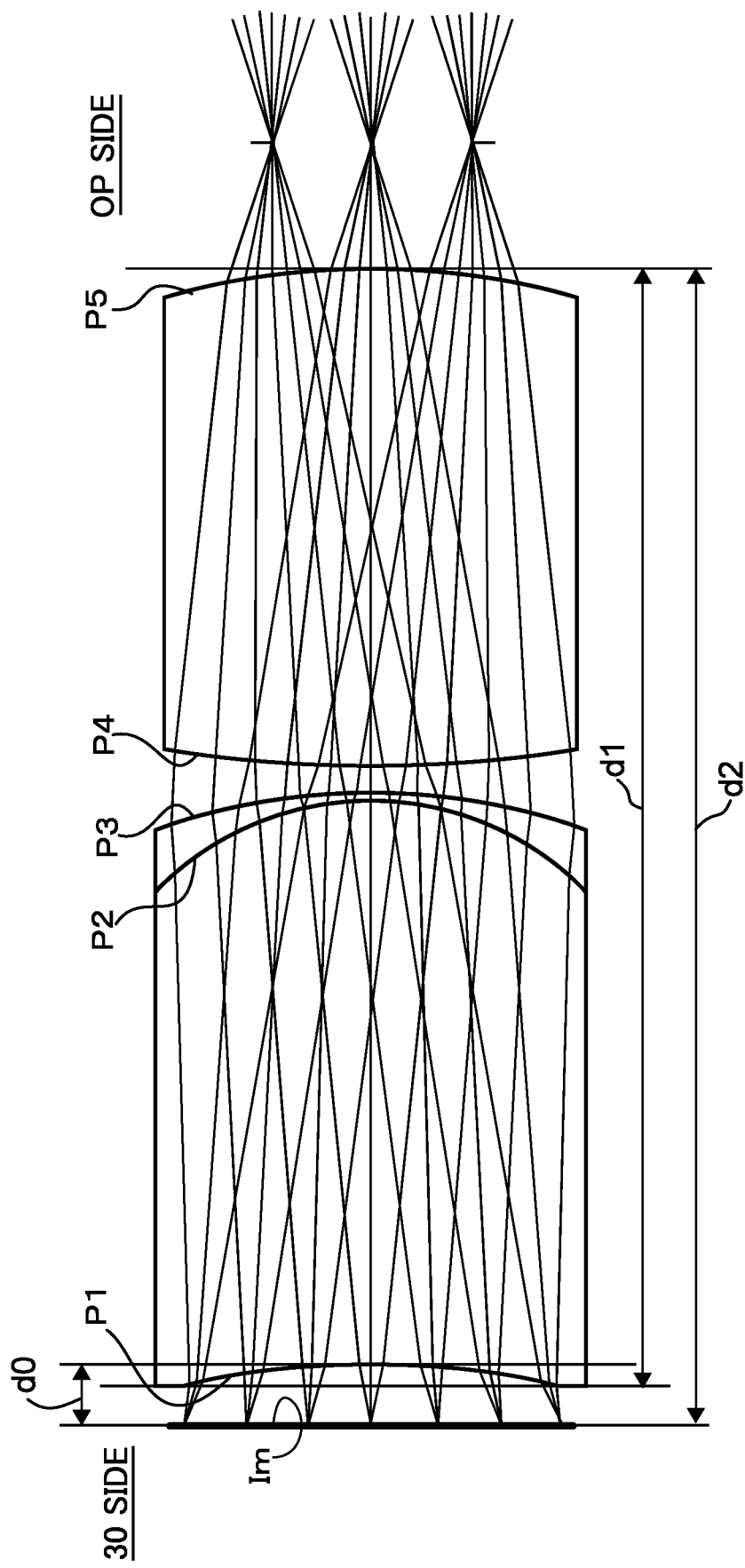
FIG. 16 is a sketch illustrating an Lens Example 7 of an optical unit.

FIG. 16 illustrates an example of a configuration of an optical unit 42 formed by a two-group, three-element lens as Lens Example 7 with different specification values to the Lens Example 4, and an example of optical paths thereof.

The optical unit 42 illustrated in FIG. 16 is formed by the two-group, three-element lens with optical surfaces of Surface Nos. P1, P2, P3, P4, P5 in sequence on progression away from the imaging image Im. In the example illustrated in FIG. 16, the optical unit 42 illustrates a case arranged with a separation of 10.0 mm as the distance d0 from the imaging image Im.

Specification values of the optical unit 42 of Lens Example 7 are listed in the following Table 7. Note that the case envisaged here is one in which the lens effective diameter of Lens Example 7 is 29.46, and the distance of the imaging image Im (distance or size of the image display region) is 30.47.

TABLE 7

| Surface No. m | Radius of Curvature r (mm) | Inter-Surface Distance d (mm) | Refractive Index nd | Dispersion vd |
| --- | --- | --- | --- | --- |
| P1 | −118.29 | 90 | 1.62041 | 60.24 |
| P2 | −45.68 | 1.0 | 1.75520 | 27.57 |
| P3 | −104.24 | 4.2 | | |
| P4 | 195.88 | 80 | 1.62041 | 60.24 |
| P5 | −120.04 | | | |

In the optical unit 42 of Lens Example 7, the value determined by the fourth condition equation (=d1/d2) is 0.97, satisfying the fourth design condition. Moreover, the value determined by the seventh condition equation (=Q) is 0.911, satisfying the seventh design condition. The optical unit 42 of Lens Example 7 accordingly enables the size of the eyebox area formed by the optical unit 42 to be increased, and also enables aberration correction for off-axis light, such as coma aberration, magnification related chromatic aberration, and distortion. Moreover, the chief light ray of the center angle of view and of the maximum angle of view can be separated at the lens surface closest to the display section 30, and a spherical surface or an aspherical surface is definable so as to independently impart appropriate refraction for both the center angle of view and the maximum angle of view.

The Lens Example 7 accordingly enables the size of the eyebox area to be increased, and also enables correction of various aberrations, and can therefore be expected to improve the image quality of images viewed by the observer OP.

Lens Example 8

Figure 17:
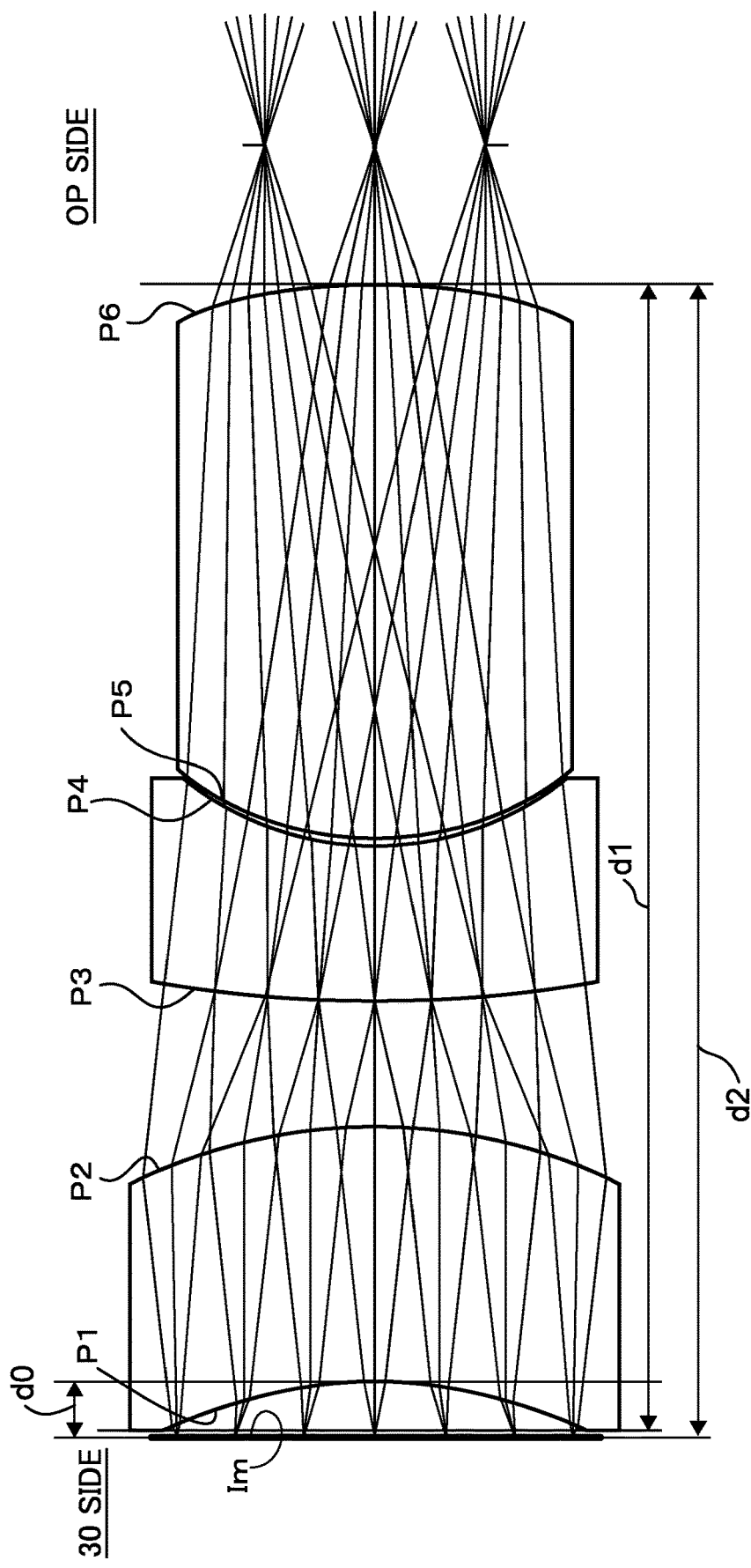
FIG. 17 is a sketch illustrating an Lens Example 8 of an optical unit.

FIG. 17 illustrates an example of a configuration of an optical unit 42 formed by a three-group, three-element lens as Lens Example 8 with different specification values to the Lens Example 5, and an example of optical paths thereof.

The optical unit 42 illustrated in FIG. 17 is formed by the three-group, three-element lens with optical surfaces of Surface Nos. P1, P2, P3, P4, P5, P6 in sequence on progression away from the imaging image Im. In the example illustrated in FIG. 17, the optical unit 42 illustrates a case arranged with a separation of 8.3 mm as the distance d0 from the imaging image Im.

Specification values of the optical unit 42 of Lens Example 8 are listed in the following Table 8. Note that the case envisaged here is one in which the lens effective diameter of Lens Example 8 is 29.27, and the distance of the imaging image Im (distance or size of the image display region) is 29.41.

TABLE 8

| Surface No. m | Radius of Curvature r (mm) | Inter-Surface Distance d (mm) | Refractive Index nd | Dispersion vd |
|---|---|---|---|---|
| P1 | −62.111 | 36.9 | 1.62041 | 60.24 |
| P2 | −75.848 | 18.1 | | |
| P3 | 205.405 | 22.2 | 1.75520 | 27.57 |
| P4 | 42.662 | 1.0 | | |
| P5 | 44.880 | 80.7 | 1.62041 | 60.24 |
| P6 | −74.596 | | | |

In the optical unit 42 of Lens Example 8, the value determined by the fourth condition equation (=d1/d2) is 0.99, satisfying the fourth design condition. Moreover, the value determined by the seventh condition equation (=Q) is 0.919, satisfying the seventh design condition. The optical unit 42 of Lens Example 8 accordingly enables the size of the eyebox area formed by the optical unit 42 to be increased, and also enables aberration correction for off-axis light such as coma aberration, magnification related chromatic aberration, and distortion. Moreover, the chief light ray of the center angle of view and of the maximum angle of view can be separated at the lens surface closest to the display section 30, and a spherical surface or an aspherical surface is definable so as to independently impart appropriate refraction for both the center angle of view and the maximum angle of view.

The Lens Example 8 accordingly enables the size of the eyebox area to be increased, and also enables correction of various aberrations, and can therefore be expected to improve the image quality of images viewed by the observer OP.

Lens Example 9

Figure 18:
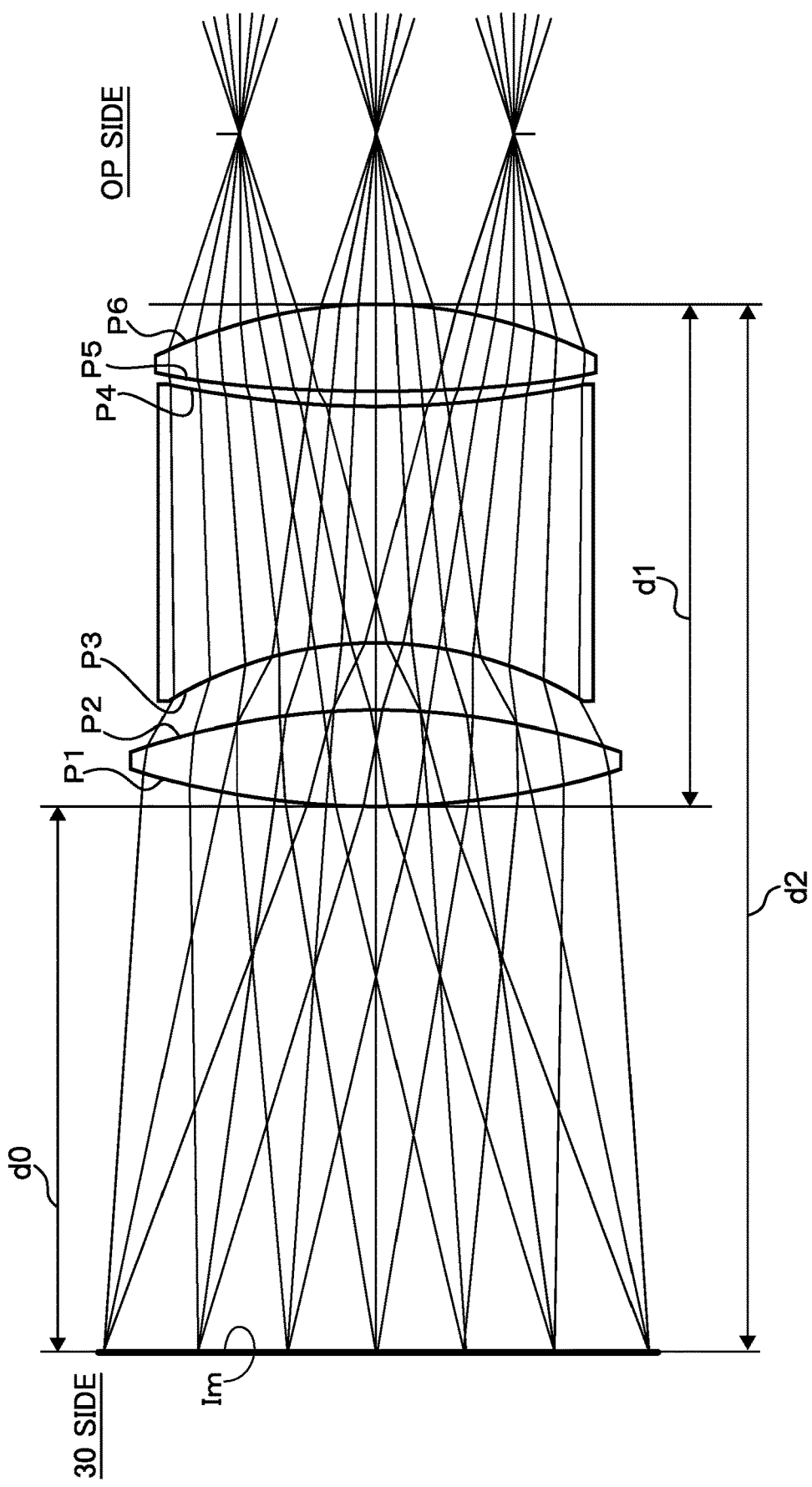
FIG. 18 is a sketch illustrating an Lens Example 9 of an optical unit.

FIG. 18 illustrates an example of a configuration of an optical unit 42 formed by a three-group, three-element lens as Lens Example 9 with different specification values to the Lens Example 5 and the Lens Example 8, and an example of optical paths thereof.

The optical unit 42 illustrated in FIG. 18 is formed by the three-group, three-element lens with optical surfaces of Surface Nos. P1, P2, P3, P4, P5, P6 in sequence on progression away from the imaging image Im. In the example illustrated in FIG. 18, the optical unit 42 illustrates a case arranged with a separation of 63.8 mm as the distance d0 from the imaging image Im.

Specification values of the optical unit 42 of Lens Example 9 are listed in the following Table 9. Note that the case envisaged here is one in which the lens effective diameter of Lens Example 9 is 27.38, and the distance of the imaging image Im (distance or size of the image display region) is 31.94.

TABLE 9

| Surface No. m | Radius of Curvature r (mm) | Inter-Surface Distance d (mm) | Refractive Index nd | Dispersion vd |
|---|---|---|---|---|
| P1 | 95.477 | 11.185 | 1.62041 | 60.24 |
| P2 | −85.687 | 7.87 | | |
| P3 | −45.443 | 27.87 | 1.70651 | 29.86 |
| P4 | 117.119 | 1.9 | | |
| P5 | 181.544 | 10.109 | 1.74397 | 44.85 |
| P6 | −56.419 | 20 | | |

In the optical unit 42 of Lens Example 9, the value determined by the fourth condition equation (=d1/d2) is 0.48, and the value determined by the seventh condition equation (=Q) is 0.572. The optical unit 42 of Lens Example 9 satisfies the seventh design condition. Accordingly, a spherical surface or an aspherical surface is definable so as to impart appropriate refraction for both the center angle of view and the maximum angle of view at the lens surface closest to the display section 30. However, the optical unit 42 of Lens Example 9 does not satisfy the fourth design condition. Accordingly, although increasing the size of the eyebox area formed by the optical unit 42 is enabled, aberration correction is difficult for off-axis light, such as coma aberration, magnification related chromatic aberration, and distortion, and aberration of the on-axis light is exacerbated by correcting aberration of the off-axis light.

Accordingly, the Lens Example 9 enables the size of the eyebox area to be increased, and although the correction of various aberration gives rise to difficult circumstances, due to spherical surfaces or aspherical surfaces being definable so as to impart appropriate refraction for both the center angle of view and the maximum angle of view, an improvement in image quality of images viewed by the observer OP can be expected in comparison to a lens that does not satisfy the seventh design condition.

As described above, configuring the optical unit 42 so as to satisfy the design conditions described above enables the optical unit 42 to increase the size of the eyebox area and also enables aberration correction for off-axis light, such as coma aberration, magnification related chromatic aberration, and distortion. Moreover, the chief light ray of the center angle of view and the chief light ray of the maximum angle of view can be separated at the lens surface closest to the display section 30, and a spherical surface or an aspherical surface is definable so as to independently impart appropriate refraction for both the center angle of view and the maximum angle of view.

In the present exemplary embodiment, the optical unit 42 is configured with the exit pupil Exp positioned on the light exit side. Accordingly, a wide eyebox area IB is formed on the light exit side of the optical unit 42, namely on the side viewed by the observer OP, thereby enabling the degrees of freedom for setting the position of the head of the observer OP to be improved.

Figure 19:
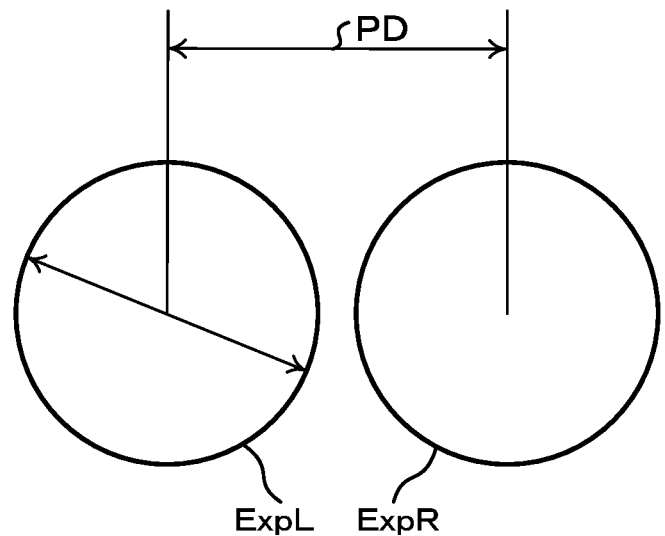
FIG. 19 is a sketch illustrating an example of an exit pupil in a display device included in an ophthalmic system according to an exemplary embodiment.

FIG. 19 illustrates an example of the exit pupils Exp in the image display device 40 according to the present exemplary embodiment.

As illustrated in FIG. 19, the exit pupils Exp of the image display device 40 are formed by a right-eye exit pupil ExpR and a left-eye exit pupil ExpL.

Moreover, the present exemplary embodiment is configured such that the positions of the exit pupils Exp are positioned on the light exit side of the optical unit 42. This accordingly enables the exit pupils of the optical unit 42 to be formed with a size corresponding to the lens diameter of the optical unit 42, enabling maximum values of the diameters of the right-eye exit pupil ExpR and the left-eye exit pupil ExpL to be enlarged to a size corresponding to the lens diameter of the optical unit 42. By positioning each of the eyes of the observer OP inside the exit pupil of the right-eye exit pupil ExpR and the left-eye exit pupil ExpL respectively, the observer OP is able to visually confirm an imaging image ImR for the right eye of the observer OP and an imaging image ImL for the left eye of the observer OP. The ophthalmic system 10 of the present exemplary embodiment accordingly does not need a mechanism to adjust the pupil distance PD, such as is installed in a binocular view microscope of related art.

The size, namely the diameter, of the right-eye exit pupil ExpR and the left-eye exit pupil ExpL is limited by the lens diameter of the optical unit 42. However, there are cases in which there is a demand for the size of the exit pupils Exp to be enlarged to give the observer OP a larger range of visibility. In such cases, the lens diameter of the optical unit 42 can be made larger than the pupil distance PD, such that portions of the optical unit 42 overlap with each other.

Namely, in cases in which the image display device 40 is configured including the right-eye optical unit 42R and the left-eye optical unit 42L, the respective diameters of the right-eye optical unit 42R and the left-eye optical unit 42L are preferably formed as diameters not greater than a distance corresponding to the pupil distance PD of the observer OP observing the imaging image (display image) Im.

In cases in which the image display device 40 is configured with at least one out of the right-eye optical unit 42R or the left-eye optical unit 42L having a diameter exceeding a distance corresponding to the pupil distance PD of the observer OP, an overlapping portion arises where the right-eye optical unit 42R and the left-eye optical unit 42L overlap. In such cases, a portion of at least one optical unit out of the right-eye optical unit 42R or the left-eye optical unit 42L may be removed (for example using a so-called D-cut) at the overlapping portion so that the right-eye optical unit 42R and the left-eye optical unit 42L do not overlap with each other.

Figure 20:
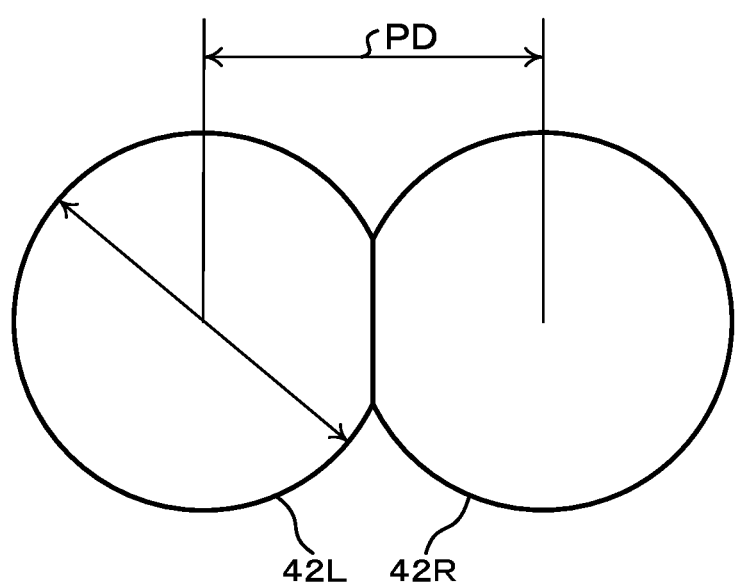
FIG. 20 is a sketch illustrating an example of a configuration of an optical unit.

FIG. 20 illustrates an example of a configuration of an optical unit 42 in which the lens diameter is larger than the pupil distance PD.

The right-eye optical unit 42R and the left-eye optical unit 42L interfere with each other in cases in which a lens diameter of the optical unit 42 is larger than the pupil distance PD. The optical units 42 may accordingly be formed by removing an interfering portion of at least one of the optical units 42 out of the right-eye optical unit 42R or the left-eye optical unit 42L. The example illustrated in FIG. 20 is of a case in which portions of the optical units 42 have been removed uniformly from the right-eye optical unit 42R and the left-eye optical unit 42L. Adopting such a configuration enables the separation between the optical axis of the right-eye optical unit 42R and the optical axis of the left-eye optical unit 42L to be maintained at a state of the pre-set pupil distance PD, and enables larger exit pupils Exp to be formed than cases in which the optical units 42 are formed with a diameter corresponding to the pupil distance PD.

Note that by forming a wide eyebox area IB externally on the exit side of the optical unit 42, the degrees of freedom for setting the position of the head of the observer OP are improved. However, there is a chance that ambient light might enter the eyes of the observer OP. In order to eliminate this, a suppression member to suppress ambient light may be provided on an optical path of ambient light to the eyes of the observer OP so as to suppress the entry of such ambient light.

Figure 21:
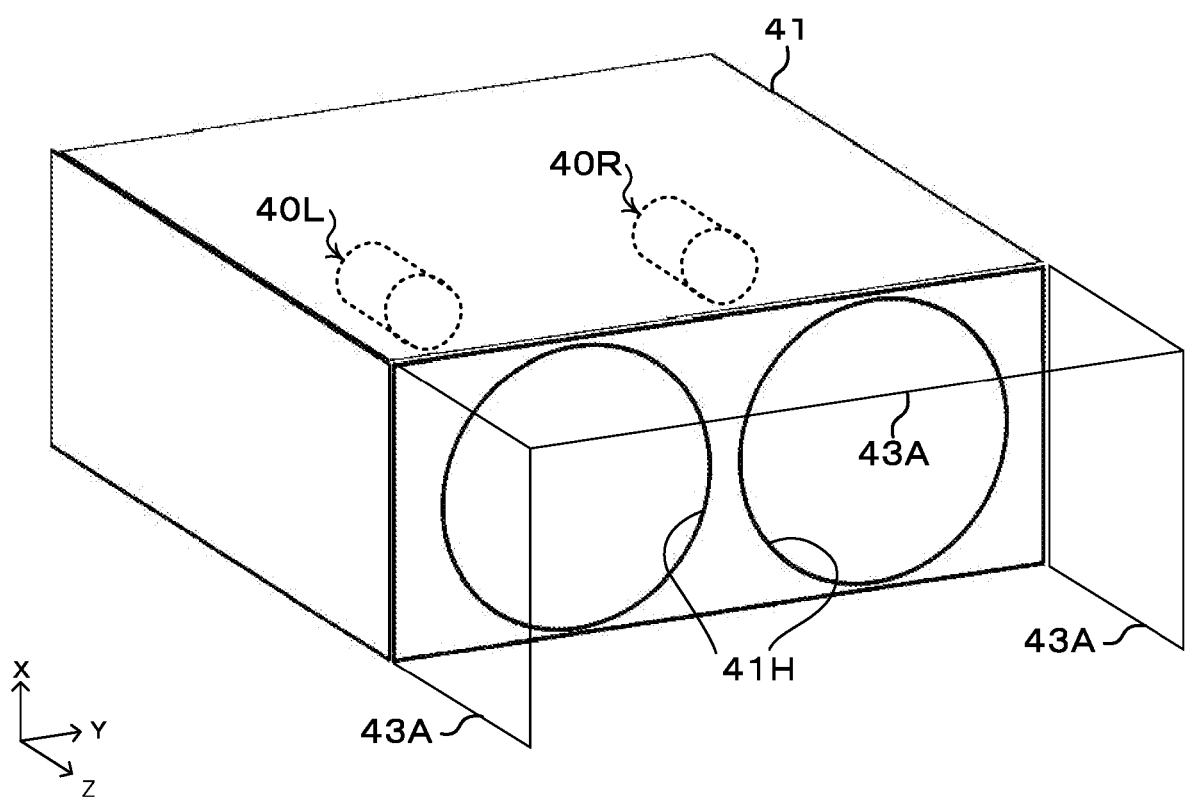
FIG. 21 is a sketch illustrating an example of a suppression member according to an exemplary embodiment.

FIG. 21 illustrates an example of a suppression member to suppress ambient light from entering the eyes of the observer OP.

As illustrated in FIG. 21, the image display device 40 according to the present exemplary embodiment is provided with the housing case 41 to house the right-eye optical unit 42R and the left-eye optical unit 42L. The housing case 41 covers at least the right-eye optical unit 42R and the left-eye optical unit 42L, and includes a function to block ambient light to the right-eye optical unit 42R and the left-eye optical unit 42L. The housing case 41 also includes respective openings 41H on the light exit side of the right-eye optical unit 42R and the left-eye optical unit 42L. The openings 41H are formed so as not to block light on the optical paths leading to the exit pupils Exp.

In the housing case 41 there is a light blocking plate 43A serving as a suppression member attached on the light exit side, namely on the observer OP side, of the openings 41H. As long as the light blocking plate 43A includes a function to suppress ambient light, the light blocking plate 43A may be configured using any optical member such as a plate to block ambient light, or using an optical member such as a neutral density (ND) filter to attenuate light transmission. Note that although in the example illustrated in FIG. 21 the light blocking plate 43A is attached at three directions, i.e. at the top and on the left and right, the light blocking plate 43A may be provided at a location where light is suppressed in at least one main direction of ambient light, or may be provided so as to cover the top and bottom and the left and right. The light blocking plate 43A is an example of a light suppression section of the present disclosure.

Figure 22:
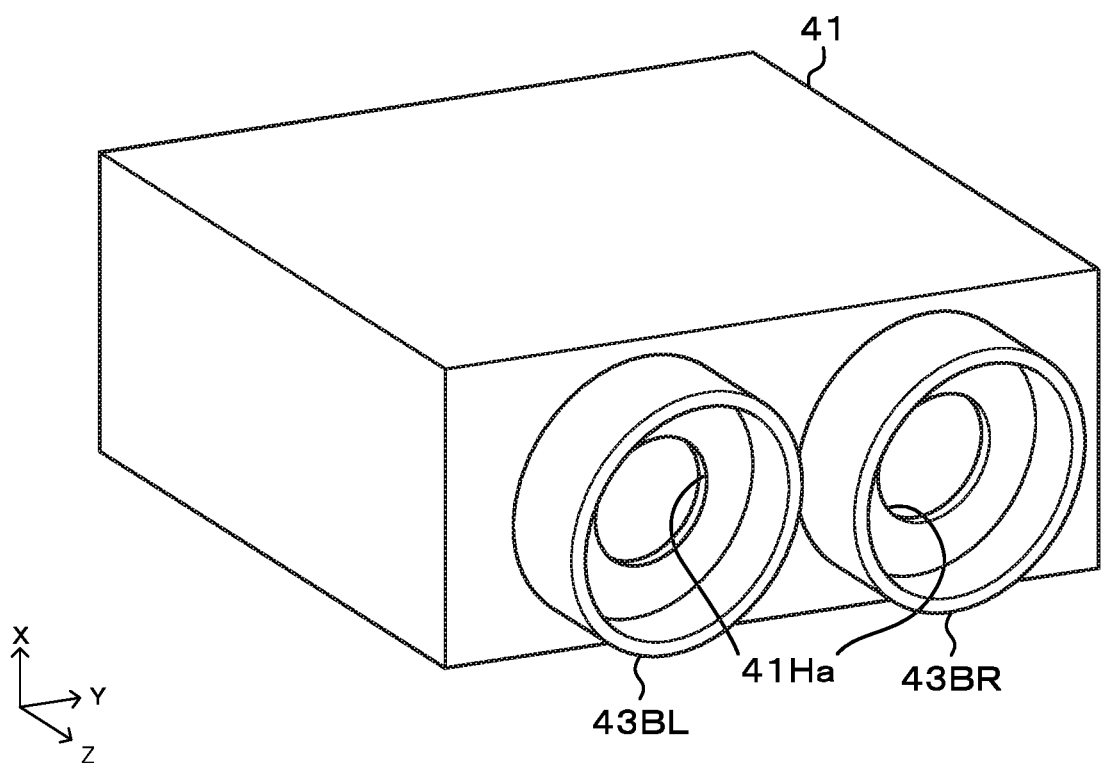
FIG. 22 is a sketch illustrating another example of suppression members according to an exemplary embodiment.

FIG. 22 illustrates another example of suppression members to suppress ambient light from entering the eyes of the observer OP.

In the example illustrated in FIG. 22, a right-eye suppression member 43BR and a left-eye suppression member 43BL are attached to the housing case 41. The suppression members 43BR, 43BL are each formed from an elastic material such as rubber in order to suppress discomfort when in contact with the head of the observer OP. Accordingly, ambient light can be suppressed by the observer OP contacting their head against the suppression members 43BR, 43BL. Note that the example illustrated in FIG. 22 illustrates an example in which the suppression members 43BR, 43BL are provided to respective openings 41Ha that have smaller diameters than the openings 41H illustrated in FIG. 21. The size of the openings 41Ha takes into consideration eye relief when the head of the observer OP has contacted the suppression members 43BR, 43BL and the openings 41Ha have a predetermined profile. Note that the size of the openings 41Ha is obviously not limited to the size illustrated in FIG. 22. The suppression members 43BR, 43BL are an example of a light suppression section of the present disclosure.

Modified Examples

Although the present exemplary embodiment has described a system (ophthalmic system) applied to an ophthalmic device as an example of an image display device according to the present disclosure, an image display device according to the present disclosure may be applied to other ophthalmic devices with stereopsis capabilities. For example, the present disclosure is applicable to another ophthalmic device for making an eyebox area IB larger and presenting a floating image, namely for providing a relayed exit pupil. Explanation follows regarding such a modified example of an image display device with larger eyebox area IB.

Figure 23:
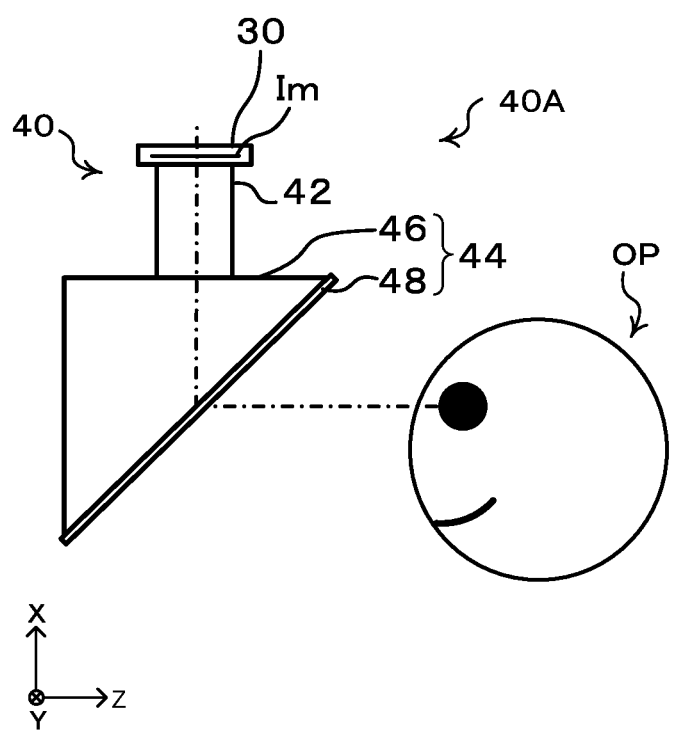
FIG. 23 is a conceptual diagram illustrating a modified example of an image display device in an ophthalmic system according to an exemplary embodiment.

FIG. 23 illustrates an example of a configuration of an image display device 40A of a modified example with enlarged eyebox area IB.

As illustrated in FIG. 23, in this modified example, a relay section 44 is attached to the image display device 40 described above to relay a pupil. The image display device 40 of the modified example images the subject eye of an observer and the periphery of the subject eye with the imaging section 20, and with the image display device 40 presents the imaging image so imaged to the observer OP using the relay section 44.

The relay section 44 includes a case 46 and an optical member 48. The image display device 40 described above that includes the optical unit 42 is attached to the case 46, and the light that has been emitted from the optical unit 42 is introduced into the case 46. Moreover, the optical member 48 is attached at the inside of the case 46 at the light exit side of the optical unit 42, so as to reflect light along a direction intersecting with the emitting optical axis of the optical unit 42 (i.e. in a direction toward the observer OP). The relay section 44 reflects the light that has been emitted from the optical unit 42 along the direction intersecting with the emitting optical axis of the optical unit 42, and forms an exit pupil at a position on the reflection side having a conjugate relationship to the exit pupil Exp of the optical unit 42. Namely, the relay section 44 relays the exit pupil Exp of the optical unit 42 by re-forming the exit pupil at the reflection side, i.e. in the direction toward the observer OP.

The case 46 of the relay section 44, to which the image display device 40 described above is attached to a non-illustrated stand, is formed independently from the imaging section 20, and is formed so as not to contact the observer OP. Forming the image display device 40A of the modified example so as not to contact the observer OP suppresses an unsettling feeling of the observer OP resulting from contact between the observer OP and the image display device 40A of the modified example.

An optical image forming element to form an equal magnification image by plural reflections using plural reflection surfaces may be employed as an example of the optical member 48 of the modified example. For example, such an optical image forming element is equipped with plural reflection members configured by plural reflection surfaces in stacked layers, with light incident to one stacked-layer end face being reflected by the reflection surfaces and emitted from the other stacked-layer end face. The plural reflection members are arranged such that the reflection surface of one reflection member and the reflection surface of another reflection member are oriented to face in intersecting directions, and such that the light emitted from a stacked-layer end face of one reflection member is incident to a stacked-layer end face of the other reflection member.

Namely, the incident light incident to the optical image forming element serving as an example of the optical member 48 is reflected by a first reflection surface, the reflected light is then reflected by a second reflection surface and then emitted from the optical image forming element. The first reflection surface and the second reflection surface are arranged in the optical image forming element such that the reflection surfaces thereof face in intersecting (orthogonal) directions. Thus when the first reflection surface and the second reflection surface are orthogonally arranged in plan view, the incident light to the optical image forming element and the light emitted from the optical image forming element are parallel when the optical image forming element is viewed in plan view. Thus plural light points that are actual points on the incident side of the optical image forming element are converged on the exit side of the optical image forming element and formed as an image of virtual points. Thus the relay section 44 re-forms the exit pupil Exp at positions having a conjugate relationship to the exit pupil Exp of the optical unit 42.

Note that the optical image forming element serving as an example of the optical member 48 can be treated as being a recursive element, or more precisely as being a recursive pass-through element. Recursive reflection is reflecting light in an opposite direction to the direction of light incident to the element using plural orthogonal reflection surfaces. However, the optical image forming element has the property of letting incident light pass through to a face on the opposite side to the incident face, and letting the light exit with changed direction when doing so, replicating light beams with plane symmetry with respect to a flat plane orthogonal to a normal to the optical image forming element. This action is one in which the progression direction of light beams is not changed in relation to the perpendicular direction of the optical image forming element when the optical image forming element performs spatial replication, and corresponds to a recursive action. The optical image forming element can accordingly be thought of as being a recursive pass-through element.

Another example of the optical image forming element is a light control panel including plural intersecting reflection surfaces as a unit optical system, with plural of these unit optical systems arrayed along the directions of a flat plane intersecting with the plural reflection surfaces. This control panel is formed by arraying plural unit optical systems configured from two substantially mutually orthogonal mirror faces that are substantially perpendicular to a specific flat plane, such as for example, two-face corner reflectors.

Moreover, although in the present exemplary embodiment a system applied to an ophthalmic device has been described as an example of an image display device according to the present disclosure, the image display device according to the present disclosure is not limited to an ophthalmic system applied to an ophthalmic device. Namely, in the present disclosure, an image display device according to the present disclosure is applicable to any device for displaying images, and an image display system according to the present disclosure is applicable to any system equipped with a device for displaying images. Explanation next follows regarding examples of image display devices to which the present disclosure is applicable, and to an application example of an image display system equipped with such image display devices.

Application Example

An application example is an example of application to a display device of an observation system for observing distant objects using an optical instrument such as binoculars, a periscope, or the like. By applying the image display device according to the present disclosure to an observation system to observe distant objects, the observer OP is able to observe distant objects in a non-contact state with the image display device 40, suppressing an unsettling feeling of the observer OP due to contact therewith. Moreover, the apparent size of an image being viewed with the optical unit 42 does not change, and so the head of the observer OP is able to move within the eyebox area. There is accordingly a larger permitted range of postures of the observer OP compared to the posture when the head of the observer OP contacts an optical instrument such as binoculars, a periscope, or the like.

Moreover, although in the present exemplary embodiment explanation has been given regarding an example of the image display device according to the present disclosure as a system applied to an ophthalmic device, the image display device according to the present disclosure may also be applied in cases enabling plural observers to view plural objects. For example, such a system may be equipped with plural of the image display devices according to the present disclosure, and the plural image display devices may display the same image as one another, or images subjected to image processing may be displayed on some of the image display devices.

Note that although exemplary embodiments related to the present disclosure have been described, the technical scope of the present disclosure is not limited to the scope described in the above exemplary embodiments. Various modifications and improvements can be made to the exemplary embodiments described above without departing from the scope of the gist of the present disclosure, and these modifications and improvements are included within the scope of the present disclosure. Moreover, all publications, patent applications and technical standards mentioned in the present specification are incorporated by reference in the present specification to the same extent as if each individual publication, patent application, or technical standard was specifically and individually indicated to be incorporated by reference.

The invention claimed is:

1. An optical unit comprising:
an optical system that includes a focal point on a light incident side at a position for setting a display image of an object and that is configured to emit light from a focal plane as parallel light; and
a housing section housing the optical system;
the optical unit being configured so as to satisfy a condition equation expressed by $IB \geq 7570$ mm$^3$ wherein IB is a viewable area where the display image is viewable,
wherein the viewable area is derived based on an effective diameter of a lens included in the optical system and based on an angle formed between a chief light ray at a maximum angle of view and an optical axis of the optical system, and
wherein the viewable area is formed so as to satisfy a condition equation expressed by $\omega \leq 50°$ wherein $\omega$ is the angle formed between the chief light ray at the maximum angle of view in the optical system and the optical axis of the optical system.

2. The optical unit of claim 1, wherein the optical system forms a pupil at a position on an exit side of the light.

3. The optical unit of claim 1, wherein the optical unit is configured such that the viewable area satisfies a condition equation expressed by $IB \geq 9000$ mm$^3$.

4. The optical unit of claim 1, wherein the optical unit is configured so as to satisfy a condition equation expressed by $d1/d2 > 0.5$ wherein, in the optical system:
d1 is a distance from an end portion of a lens surface on the light incident side to an end portion of a lens surface on a light exit side; and
d2 is a distance from a position of the display image to the end portion of the lens surface on the light exit side.

5. The optical unit of claim 1, wherein the optical system is formed such that the chief light ray incident to a first lens at a maximum angle of view from light of the display image pass through at positions at a greater diameter than ½ an effective diameter of the first lens.

6. The optical unit of claim 1, wherein the optical system is configured so as to satisfy a condition equation expressed by $½ < D \cdot (1 - d3/P\text{in})/\varphi < 1$ wherein:
$\varphi$ is an effective diameter of a first lens incident with light of the display image;
D is a distance of the display image;
d3 is a distance from a position of the display image to the first lens; and
Pin is a distance from the position of the display image to a position of an incident pupil of the optical system.

7. The optical unit of claim 5, wherein the first lens is a lens to which light of the display image is first incident.

8. The optical unit of claim 1, wherein the optical unit is configured so as to form a focal length of light in the optical system that is from 25 mm to 100 mm and that satisfies a condition equation expressed by $f \leq (D/2)/\sin \omega$ wherein:
f is the focal length of the optical system;
$\omega$ is an angle formed between the chief light ray at a maximum angle of view and an optical axis of the optical system; and
D is a distance of the display image.

9. The optical unit of claim 6, wherein the first lens has a light ray separation at a lens surface of the first lens such that, of light from the focal plane, a chief light ray of on-axis light do not overlap with chief light rays of off-axis light.

10. An optical device comprising a plurality of the optical unit of claim 1.

11. The optical device of claim 10, wherein the plurality of optical units are fixed such that optical axes of the plurality of optical units are parallel to each other.

12. The optical device of claim 10, further comprising a light suppression section arranged at an exit side of light from the plurality of optical units and configured to suppress external light from reaching at least one of the plurality of optical units.

13. An image display system comprising:
an optical device comprising:
a left-side optical system that includes a focal point on a light incident side at a position for setting a left-eye display image as a display image of an object, and that is configured to emit light from a focal plane as parallel light and to form a left-eye viewable area where the left-eye display image is viewable;
a right-side optical system that includes a focal point on a light incident side at a position for setting a right-eye display image different from the left-eye display image, and that is configured to emit light from a focal plane as parallel light and to form a right-eye viewable area where the right-eye display image is viewable; and a housing section to house the left-side optical system and the right-side optical system;

an imaging section configured to image the object; and an arm section on which the imaging section is disposed, wherein the optical device being configured, in at least one optical system of the left-side optical system or the right-side optical system, so as to satisfy a condition equation expressed by $d1/d2 > 0.5$ wherein:

d1 is a distance from an end portion of a lens surface on a light incident side to an end portion of a lens surface on a light exit side, and d2 is a distance from a position of the display image to the end portion of the lens surface on the light exit side.

14. The image display system of claim 13, wherein the optical device is configured so as to satisfy a condition equation expressed by $IB \geq 7570 \text{ mm}^3$ wherein IB is a viewable area where the display image is viewable.

15. The image display system of claim 13, wherein the optical device further comprising a display section configured to display the display image of the object.

16. The image display system of claim 13, wherein the optical device is able to move independently from the imaging section.

* * * * *